United States Patent
Oldfield et al.

(10) Patent No.: US 12,097,324 B2
(45) Date of Patent: Sep. 24, 2024

(54) APPARATUS FOR CONTROLLING GAS DELIVERY TO A PATIENT

(71) Applicant: Fisher & Paykel Healthcare Limited, Auckland (NZ)

(72) Inventors: Samantha Dale Oldfield, Auckland (NZ); Milanjot Singh Assi, Auckland (NZ); Dexter Chi Lun Cheung, Auckland (NZ); Callum James Thomas Spence, Auckland (NZ); Alicia Jerram Hunter Evans, Auckland (NZ); Craig Karl White, Auckland (NZ); Matthew Jon Payton, Auckland (NZ); Thomas Heinrich Barnes, Surrey (GB)

(73) Assignee: Fisher & Paykel Healthcare Limited, Auckland (NZ)

( * ) Notice: Subject to any disclaimer, the term of this patent is extended or adjusted under 35 U.S.C. 154(b) by 265 days.

(21) Appl. No.: 15/563,097

(22) PCT Filed: Mar. 31, 2016

(86) PCT No.: PCT/IB2016/051818
§ 371 (c)(1),
(2) Date: Sep. 29, 2017

(87) PCT Pub. No.: WO2016/157104
PCT Pub. Date: Oct. 6, 2016

(65) Prior Publication Data
US 2018/0071469 A1   Mar. 15, 2018

Related U.S. Application Data

(60) Provisional application No. 62/140,612, filed on Mar. 31, 2015, provisional application No. 62/140,638, filed on Mar. 31, 2015.

(51) Int. Cl.
*A61M 16/00* (2006.01)
*A61B 1/267* (2006.01)
(Continued)

(52) U.S. Cl.
CPC ........... *A61M 16/022* (2017.08); *A61B 1/267* (2013.01); *A61M 11/007* (2014.02);
(Continued)

(58) Field of Classification Search
CPC ............ A61M 16/022; A61M 16/0003; A61M 16/1005; A61M 16/201; A61M 16/04;
(Continued)

(56) References Cited

U.S. PATENT DOCUMENTS 3,974,828 A * 8/1976 Bird .................. A61M 16/0012
128/204.25
4,535,767 A    8/1985 Tiep
(Continued)

FOREIGN PATENT DOCUMENTS

GB          2 368 533      5/2002
WO    WO 2003/041780      5/2003
(Continued)

OTHER PUBLICATIONS

Jul. 27, 2016 International Search Report for International Application No. PCT/IB2015/051818 filed on Mar. 31, 2016.

*Primary Examiner* — Elliot S Ruddie
(74) *Attorney, Agent, or Firm* — Knobbe Martens Olson & Bear LLP

(57) ABSTRACT

This invention relates to, among other embodiments, methods and apparatus/systems for controlling gases delivery to a patient, such as via a patient interface. Such methods comprising receiving an input relating to either a patient's breathing phase and/or another patient parameter, controlling a flow of gases to be delivered to the patient and the
(Continued)

Expiration inclusion in said flow of gases of a supplementary gas, wherein the amount of supplementary gas provided to the patient is substantially synchronized with respect to the patient's breathing phase and/or another patient parameter.

29 Claims, 17 Drawing Sheets

(51) Int. Cl.
    *A61M 11/00*     (2006.01)
    *A61M 16/04*     (2006.01)
    *A61M 16/06*     (2006.01)
    *A61M 16/08*     (2006.01)
    *A61M 16/10*     (2006.01)
    *A61M 16/12*     (2006.01)
    *A61M 16/16*     (2006.01)
    *A61M 16/20*     (2006.01)

(52) U.S. Cl.
CPC .... *A61M 16/0003* (2014.02); *A61M 16/0066* (2013.01); *A61M 16/04* (2013.01); *A61M 16/0493* (2014.02); *A61M 16/0666* (2013.01); *A61M 16/0672* (2014.02); *A61M 16/0677* (2014.02); *A61M 16/0875* (2013.01); *A61M 16/1005* (2014.02); *A61M 16/104* (2013.01); *A61M 16/12* (2013.01); *A61M 16/16* (2013.01); *A61M 16/201* (2014.02); *A61M 16/202* (2014.02); *A61M 16/204* (2014.02); *A61M 2016/0018* (2013.01); *A61M 2016/0021* (2013.01); *A61M 2016/0027* (2013.01); *A61M 2016/003* (2013.01); *A61M 16/0434* (2013.01); *A61M 16/0461* (2013.01); *A61M 16/0688* (2014.02); *A61M 2016/1025* (2013.01); *A61M 2016/1035* (2013.01); *A61M 2202/0208* (2013.01); *A61M 2202/0241* (2013.01); *A61M 2202/025* (2013.01); *A61M 2202/0275* (2013.01); *A61M 2202/0283* (2013.01); *A61M 2202/03* (2013.01); *A61M 2202/0488* (2013.01); *A61M 2205/05* (2013.01); *A61M 2205/18* (2013.01); *A61M 2205/3303* (2013.01); *A61M 2205/3334* (2013.01); *A61M 2205/50* (2013.01); *A61M 2230/205* (2013.01); *A61M 2230/432* (2013.01); *A61M 2230/60* (2013.01); *A61M 2230/65* (2013.01)

(58) Field of Classification Search
CPC ............ A61M 16/0666; A61M 16/104; A61M 16/12; A61M 2016/0018; A61M 2202/0208; A61M 2202/0241; A61M 2202/025; A61M 2202/0275; A61M 2202/0283; A61M 2205/3303; A61M 11/007; A61M 16/0066; A61M 16/0493; A61M 16/0672; A61M 16/0677; A61M 16/0875; A61M 16/16; A61M 16/202; A61M 16/204; A61M 16/0434; A61M 16/0461; A61M 16/0688; A61M 2016/0021; A61M 2016/0027; A61M 2016/003; A61M 2016/1025; A61M 2016/1035; A61M 2202/03; A61M 2202/0488; A61M 2205/05; A61M 2205/18; A61M 2205/3334; A61M 2205/50; A61M 2230/205; A61M 2230/432; A61M 2230/60; A61M 2230/65; A61B 1/267

See application file for complete search history.

(56) References Cited

U.S. PATENT DOCUMENTS

| | | | |
|---|---|---|---|
| 4,821,709 A * | 4/1989 | Jensen | A61M 16/0096 128/204.21 |
| 6,192,884 B1 | 2/2001 | Vann et al. | |
| 6,581,599 B1 * | 6/2003 | Stenzler | A61M 16/203 128/204.23 |
| 7,105,008 B2 | 9/2006 | Maryanka | |
| 8,910,635 B2 | 12/2014 | Pierro et al. | |
| 11,298,494 B2 | 4/2022 | Barraclough et al. | |
| 2002/0053286 A1 | 5/2002 | Czabala | |
| 2003/0094178 A1 | 5/2003 | McAuley et al. | |
| 2005/0028816 A1 * | 2/2005 | Fishman | A61M 16/0051 128/200.24 |
| 2005/0028822 A1 | 2/2005 | Sleeper et al. | |
| 2005/0217671 A1 * | 10/2005 | Fisher | A61B 5/083 128/204.18 |
| 2006/0042631 A1 * | 3/2006 | Martin | A61B 5/0836 128/207.18 |
| 2006/0174889 A1 | 8/2006 | Noble | |
| 2006/0207597 A1 | 9/2006 | Wright | |
| 2008/0047559 A1 | 2/2008 | Fiori | |
| 2008/0051674 A1 * | 2/2008 | Davenport | A61M 16/161 128/207.18 |
| 2009/0151719 A1 * | 6/2009 | Wondka | A61M 16/0858 128/203.12 |
| 2011/0125052 A1 | 5/2011 | Davenport et al. | |
| 2012/0017909 A1 * | 1/2012 | Porges | A61M 16/12 128/205.25 |
| 2012/0240924 A1 | 9/2012 | Rustad | |
| 2013/0160766 A1 * | 6/2013 | Malouf | A61M 16/0833 128/203.12 |
| 2013/0340752 A1 | 12/2013 | Landis et al. | |
| 2014/0290668 A1 | 10/2014 | Thornton et al. | |
| 2018/0078726 A1 | 3/2018 | Barraclough et al. | |
| 2022/0323704 A1 | 10/2022 | Barraclough et al. | |

FOREIGN PATENT DOCUMENTS

| | | |
|---|---|---|
| WO | WO 2007/063532 | 6/2007 |
| WO | WO 2008/092021 | 7/2008 |
| WO | WO 2009/123977 | 10/2009 |
| WO | WO 2012/040792 | 4/2012 |
| WO | WO 2015/049538 | 4/2015 |

* cited by examiner

APPARATUS FOR CONTROLLING GAS DELIVERY TO A PATIENT

TECHNICAL FIELD

The present disclosure relates to delivering gas to patients using a high flow apparatus/source and systems for conserving gases being supplied to a patient, and/or to methods and systems for providing a flow therapy to treat lung recruitment or preventing lung collapses caused by various reasons.

BACKGROUND ART

Patients may lose respiratory function during anaesthesia, or sedation, or more generally during certain medical procedures. Prior to a medical procedure a patient may be pre-oxygenated by a medical professional to provide a reservoir of oxygen saturation, and this pre-oxygenation is generally carried out with a bag and a face mask. Once under general anaesthesia, patients must be intubated to ventilate the patient. In some cases, intubation is completed in 30 to 60 seconds, but in other cases, particularly if the patient's airway is difficult to traverse (for example, due to cancer, severe injury, obesity or spasm of the neck muscles), intubation will take significantly longer. While pre-oxygenation provides a buffer against declines in oxygen saturation, for long intubation procedures, it is necessary to interrupt the intubation process and reapply the face mask to increase the patient's oxygen saturation to adequate levels. The interruption of the intubation process may happen several times for difficult intubation processes, which is time consuming and puts the patient at severe health risk. After approximately three attempts at intubation the medical procedure will be abandoned.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

SUMMARY

It may be an object of one or more of the disclosed embodiments to provide for a method and/or system or apparatus for assisting in preserving oxygen and/or other gases being supplied to a patient, or for diverting at least some of the gases being supplied to a patient away from the patient at particular phases, which will go at least some way towards addressing the foregoing problems or which will at least provide the public or industry with a useful choice.

In an alternative, it may be an object of one or more of the disclosed embodiments to provide for a method and/or systems or apparatus for assisting in preventing and/or treating atelectasis and/or for lung recruitment in patients with diminished respiratory drive, which will go at least some way towards addressing the foregoing problems or which will at least provide the public or industry with a useful choice.

In accordance with a first embodiment disclosed herein, there is provided an apparatus for controlling gas delivered to a patient comprising: a gas line connected or connectable to a flow source, a gas reservoir, a patient interface, a valve to optionally: fluidly couple, the gas line to the reservoir, and fluidly couple, the gas line and/or reservoir (directly or indirectly) to the patient interface, a controller that receives input relating to patient breathing, wherein the controller: during patient expiration, controls the valve to couple the gas line to the reservoir, and during patient inspiration controls the valve to couple the gas line and/or reservoir to (directly or indirectly) the patient interface.

The controller during patient expiration may control the flow generator to couple gas flow to (directly or indirectly) the patient interface.

The controller during patient inspiration may control the flow generator to couple gas flow to (directly or indirectly) the patient interface.

In accordance with a second embodiment disclosed herein, there is provided an a method of controlling gas delivered to a patient comprising: receiving input on patient breathing, controlling a valve to couple a flow source to a gas reservoir during patient expiration, controlling a valve to couple: the flow source to (directly or indirectly) a patient interface, and/or the gas reservoir to (directly or indirectly) the patient interface, during patient inspiration.

During patient expiration, the method may further comprise controlling a flow generator to supply gas flow (directly or indirectly) to the patient interface.

During patient inspiration, the method may further comprise controlling a flow generator to supply gas flow (directly or indirectly) to the patient interface.

In accordance with a third embodiment disclosed herein, there is provided an apparatus for controlling gas delivered to a patient comprising: a gas line connected or connectable to a flow source, a gas reservoir, and a controller configured to receive input on patient breathing, direct gas flow from a flow source to the gas reservoir during expiration, and directing gas flow and from the flow source/or gas from the reservoir (directly or indirectly) to a patient interface during inspiration.

In accordance with a fourth embodiment disclosed herein, there is provided an a method of controlling gas delivered to a patient comprising: receiving input on patient breathing, directing gas flow from a flow source to a gas reservoir during expiration, and directing gas flow and from the flow source/or gas from the reservoir (directly or indirectly) to a patient interface during inspiration.

In accordance with a fifth embodiment disclosed herein, there is provided an apparatus for controlling gas delivered to a patient comprising:
  a gas line connected or connectable to a flow source,
  a gas reservoir,
  a patient interface,
  a valve configured to:
    (in a first configuration) fluidly couple the gas line to the reservoir, and
    (in a second configuration) fluidly couple, the gas line and/or reservoir (directly or indirectly) to the patient interface,
  a controller that receives input relating to a patient's breathing phases and/or another patient parameter,
  wherein the controller is configured to:
    in response to the input received, control the valve to the first configuration to couple the gas line to the reservoir during a patient breathing phase of expiration and/or said another patient parameter, and
  in response to the input received, control the valve to the second configuration to couple the gas line and/or reservoir to (directly or indirectly) the patient interface.

The controller during patient expiration may control the flow generator to couple gas flow to (directly or indirectly) the patient interface.

The controller during patient inspiration may control the flow generator to couple gas flow to (directly or indirectly) the patient interface.

In accordance with a sixth embodiment described herein, there is provided a method of controlling gas delivered to a patient comprising: receiving input on patient breathing, controlling a valve to couple a flow source to a gas reservoir during patient expiration, controlling a valve to couple: the flow source to (directly or indirectly) a patient interface, and/or the gas reservoir to (directly or indirectly) the patient interface, during patient inspiration.

During patient expiration, the method may further comprise controlling a flow generator to supply gas flow (directly or indirectly) to the patient interface.

During patient inspiration, the method may further comprise controlling a flow generator to supply gas flow (directly or indirectly) to the patient interface.

In accordance with a seventh embodiment described herein, there is provided an apparatus for controlling gas delivered to a patient comprising: a gas line connected or connectable to a flow source, a gas reservoir, and a controller configured to receive input on patient breathing, direct gas flow from a flow source to the gas reservoir during expiration, and directing gas flow and from the flow source/or gas from the reservoir (directly or indirectly) to a patient interface during inspiration.

In accordance with an eighth embodiment described herein, there is provided a method of controlling gas delivered to a patient comprising: receiving input on patient breathing, directing gas flow from a flow source to a gas reservoir during expiration, and directing gas flow and from the flow source/or gas from the reservoir (directly or indirectly) to a patient interface during inspiration.

In accordance with a ninth embodiment described herein, there is provided an apparatus or system for controlling gas to be delivered to a patient comprising:
  a gas line connected or connectable to a flow source,
  a gas reservoir,
  a patient interface,
  a valve to optionally:
    fluidly couple, the gas line to the reservoir, and
    fluidly couple, the gas line and/or reservoir (directly or indirectly) to the patient interface,
  a controller that receives input relating to either a patient's breathing phase and/or another patient parameter,
  wherein the controller:
    during patient expiration, controls the valve to couple the gas line to the reservoir, and
    during patient inspiration controls the valve to couple the gas line and/or reservoir to (directly or indirectly) the patient interface.

The apparatus or system may further comprise a flow generator, wherein the controller during a patient's breathing phase of expiration controls the flow generator to couple gas flow to (directly or indirectly) the patient interface.

The apparatus or system may further comprise a flow generator, wherein the controller during a patient's breathing phase of inspiration controls the flow generator to couple gas flow to (directly or indirectly) the patient interface.

The flow generator may be controlled to provide gas flow to the patient interface at or above the patient's inspiratory demand, such as above the patient's PEAK inspiratory flow (PIF) demand.

The flow source may provide a source of supplementary gas, the supplementary gas being one or more of: oxygen, helium and oxygen (heliox), anaesthetics, analgesics, nitric oxide, nitrous oxide.

The apparatus may comprise a gas line connected or connectable to a flow source, a gas reservoir, and a controller configured to receive input on a patient's breathing phase, the gas line to direct gas flow from a flow source to the gas reservoir during a patient's expiration phase, and directing gas flow from the flow source and/or gas from the reservoir (directly or indirectly) to a patient interface during a patient's inspiration phase.

The reservoir may delivers supplementary gas to the patient interface during the patient's inspiration phase.

Supplementary gas is delivered from the reservoir as a bolus during the patient's inspiration phase.

In accordance with a tenth embodiment disclosed herein, there is provided a dispensing assembly for delivering a surfactant to a user, comprising:
  a container or reservoir for storing the surfactant, the container comprises an opening or an outlet allowing the surfactant to be dispensed from the container,
  an associated dispensing mechanism configured to cause the container to dispense the surfactant,
  a tube or conduit or other fluid passage for delivering the surfactant to the user, the tube comprises a first end which is in fluid communication with the opening of the container, and a second end which is, in-use, to extend into an airway (or the body) of the user, at the first and/or the second end of the tube there is an orifice which has a dimension configured to cause nebulisation of the surfactant as it is delivered to the user via the tube.

The dispensing mechanism may comprise a plunger reciprocally and at least partially received within the container, the movement of the plunger relative to the container causes the container to dispense surfactant from or through the opening.

The dispensing assembly may comprise a flexible bag or a pouch for storing the surfactant, the bag or the pouch is replacably located in, or housed by, the container.

The bag or pouch is pierced through by the first end of the end to release the surfactant into the tube.

The dispensing assembly may further comprise a patient interface, such as a nasal interface, for conveying gases to the user, the tube passes through the interface and extends out from a gas outlet of the interface.

In accordance with an eleventh embodiment disclosed herein, there is provided a method of delivering a gas composition to a user for preventing or treating atelectasis comprising the steps of:
  delivering a first concentration of oxygen to a user for a predetermined period, and
  delivering intermittent periods of a second concentration of oxygen to the user, wherein the second oxygen concentration is lower than the first oxygen concentration.

The first concentration of oxygen may be up to about 100% oxygen, wherein the second oxygen concentration comprises up to about 80% oxygen supplemented with nitrogen (for example, may be about 20% nitrogen), and the second oxygen concentration is delivered to the patient for up to about 1 minute, or up to about 30 seconds, or is about 10-30 seconds of delivery.

The second concentration of oxygen may comprise about 80% oxygen supplemented with helium (for example may be about 20% helium, or may be a combination of helium with one or more other gases, such as nitrogen).

In accordance with a twelfth embodiment disclosed herein, there is provided a method of preventing or treating atelectasis comprising providing a flow of oxygen gases to a user during pre-oxygenation, wherein the oxygen gases has an oxygen concentration of less than about 100% or may be less than about 80%.

The oxygen concentration may be further reduced after a lung recruitment manoeuvre to not more than about 40%, optionally to increase the time before atelectasis is likely to recur in the patient.

In accordance with an eighth embodiment disclosed herein, there is provided a method of preventing or treating atelectasis by delivering a high flow of oxygen gases during pre-oxygenation intubation attempts.

The high flow of oxygen gases may be delivered to a user down a laryngoscope and/or an endotracheal tube.

The high flow of gases may be provided to the user at or near the end of an expiration attempt.

In accordance with a thirteenth embodiment disclosed herein, there is provided a method of preventing and/or treating atelectasis by performing a lung recruitment manoeuvre on a user.

The lung recruitment manoeuvre may comprise adjusting the flow/pressure of the flow of gases delivered to the patient.

The method may further comprise delivering high frequency oscillations through respiratory support.

The method may further comprise delivering a higher than normal gas flow rate to the user for a set period and then reduce the gas flow rate to the normal treatment level.

The method may further comprise providing a range of elevated gas flow rates to the user and then reducing the gas flow rates to normal treatment level before it is increased to a higher gas flow rate again.

The manoeuvre may be initiated by a patient monitoring signal.

In accordance with a fourteenth embodiment disclosed herein, there is provided a user interface used for performing lung recruitment manoeuvres, the interface comprising a seal which can be selectively activated or engaged to create or form a seal between the user interface and the user's nose and/or mouth.

The seal may be an inflatable seal.

The user interface may be a nasal cannula and the seal may be located on or about an exterior of at least one nasal prong or each of a nasal prong associated with said nasal cannula.

The user interface may be a mouthpiece (such as a bite-block) having a passage which can be selectively opened or closed.

A seal may be located within the passage and when the seal may be inflatable to close the passage off.

In accordance with a fifteenth embodiment disclosed herein, there is provided a method of controlling gases delivery to a patient (such as via a patient interface), the method comprising:
  delivering a first concentration of oxygen or supplementary gas to a patient for a pre-determined period, and
  delivering intermittent periods of a second concentration or supplementary gas of oxygen to the user, wherein the second oxygen concentration is lower than the first oxygen concentration.

The first concentration of oxygen or supplementary gas may be up to about 100% oxygen or supplementary gas, wherein the second oxygen concentration may comprise up to about 80% oxygen or supplementary gas supplemented with nitrogen (for example, may be about 20% nitrogen), and the second oxygen or supplementary gas concentration may be delivered to the patient for up to about 1 minute, or up to about 30 seconds, or may be about 10-30 seconds of delivery.

The second concentration of oxygen or supplementary gas may comprise about 80% oxygen or supplementary gas supplemented with helium (for example may be about 20% helium or supplementary gas, or may be a combination of helium or supplementary gas with one or more other gases, such as nitrogen).

A flow of oxygen gases may be provided to a patient during pre-oxygenation, wherein the oxygen gases has an oxygen concentration of less than about 100% or may be less than about 80%.

The oxygen concentration may be further reduced after a lung recruitment manoeuvre to not more than about 40%, optionally to increase the time before atelectasis is likely to recur in the patient.

A high flow of oxygen gases may be delivered to a patient during pre-oxygenation intubation attempts.

The high flow of oxygen gases may be delivered to a patient through a laryngoscope and/or an endotracheal tube.

The high flow of gases may be provided to the patient at or near the end of an expiration attempt.

The method may comprise performing a lung recruitment manoeuvre on a user, wherein the lung recruitment manoeuvre comprises adjusting the flow/pressure of the flow of gases delivered to the patient.

The method may comprise delivering high frequency oscillations through respiratory support.

The method may comprise delivering a higher than normal gas flow rate to the patient for a set period and then reduce the gas flow rate to a normal treatment level.

The method may comprise providing a range of elevated gas flow rates to the patient and then reducing the gas flow rates to a normal treatment level before it is increased to a higher gas flow rate again.

The manoeuvre may be initiated by a patient monitoring signal.

The method may be for preventing or treating atelectasis

The oxygen gases may have an oxygen concentration of less than about 100% or may be less than about 80% during the expiration phase of a patient's breathing cycle.

In accordance with a sixteenth embodiment disclosed herein, there is provided an apparatus or system for controlling gases delivery to a patient (such as via a patient interface), the apparatus or system comprising:
  a controller,
  an interface, to provide gases to a patient
  an oxygen source or a source of supplementary gas,
  a valve connected between the oxygen source or the source of supplementary gas and the patient interface, the valve configured to control the concentration of oxygen or the supplementary gas provided to the patient interface,
  wherein the controller controls the valve to deliver a first concentration of oxygen or supplementary gas to a patient for a pre-determined period, and
  wherein, after the pre-determined period, the controller controls the valve to deliver intermittent periods of a second concentration of oxygen or supplementary gas to the user, wherein the second oxygen or supplementary gas concentration is lower than the first oxygen or supplementary gas concentration.

A flow generator may be connected to the patient interface (such as via a gases line), the flow generator may be configured to provide a flow of gases to a patient interface.

The first concentration of oxygen or supplementary gas may be up to about 100% oxygen or supplementary gas, wherein the second oxygen or supplementary gas concentration may comprise up to about 80% oxygen or supplementary gas supplemented with nitrogen (for example, may be about 20% nitrogen), and the second oxygen or supplementary gas concentration may be delivered to the patient for up to about 1 minute, or up to about 30 seconds, or may be about 10-30 seconds of delivery.

The second concentration of oxygen or supplementary gas may comprise about 80% oxygen or supplementary gas supplemented with helium (for example may be about 20% helium, or may be a combination of helium or supplementary gas with one or more other gases, such as nitrogen).

A flow of oxygen or supplementary gas gases may be provided to a patient during a pre-oxygenation phase or a phase during which the supplementary gas is to be provided to the patient, wherein the oxygen gases or supplementary gas has an oxygen or supplementary gas concentration of less than about 100% or may be less than about 80%.

The oxygen or supplementary gas concentration may be further reduced after a lung recruitment manoeuvre to not more than about 40%, optionally to increase the time before atelectasis is likely to recur in the patient.

A high flow of oxygen or supplementary gas gases may be delivered to a patient during pre-oxygenation intubation attempts.

The high flow of oxygen or supplementary gas gases may be delivered to a patient through a laryngoscope and/or an endotracheal tube.

The high flow of gases may be provided to the patient at or near the end of an expiration attempt.

The system may perform a lung recruitment manoeuvre on a user, wherein the lung recruitment manoeuvre comprises adjusting the flow/pressure of the flow of gases delivered to the patient.

The system may deliver high frequency oscillations through respiratory support.

The system may deliver a higher than normal gas flow rate to the patient for a set period and then reduce the gas flow rate to a normal treatment level.

The system may provide a range of elevated gas flow rates to the patient and then reducing the gas flow rates to a normal treatment level before it is increased to a higher gas flow rate again.

The manoeuvre may be initiated by a patient monitoring signal.

The system may help to prevent or treat atelectasis

In accordance with a seventeenth embodiment disclosed herein, there is provided a method of controlling gases delivery to a patient via a patient interface, the method comprising:
  receiving an input relating to either a patient's breathing phase and/or another patient parameter,
  controlling a flow of gases to be delivered to the patient and the inclusion in said flow of gases of a supplementary gas,
  wherein the amount of supplementary gas provided to the patient is substantially synchronized with respect to the patient's breathing phase and/or another patient parameter.

The patient may receive a lesser amount of said supplementary gas during an expiration phase of the patient's breathing phase relative to an inspiration phase of the patient's breathing phase.

The patient may receive a greater amount of said supplementary gas during an inspiration phase of the patient's breathing phase relative to an expiration phase of the patient's breathing phase.

A patient's breathing phase may be determined by a measured indicator of a patient's breathing phase, optionally the indicator is one or more of: a pressure in an airway of the patient, a patient's chest movement, a $CO_2$ measurement in or near an airway of the patient, oxygen saturation, sensors for detecting patient breathing.

The supplementary gas may be wherein the supplementary gas is one or more of: oxygen, helium and oxygen (heliox), anaesthetics, analgesics, nitric oxide, nitrous oxide.

The method may receive input relating to another patient parameter comprising a measurable attribute of a patient.

A valve may be actuated to allow a supply of the supplementary gas during an inspiration phase of the patient's breathing phase.

The flow of gases to be delivered to the patient may be maintained at a substantially constant flow rate throughout different phases of a patient's breathing phases.

The flow of gas to be delivered to the patient may be substantially synchronized with a patient's breathing phase or another patient parameter.

The flow of gases to be delivered to the patient may be of a greater flow rate during a patient's inspiration phase and a relatively lower flow rate during a patient's expiration phase.

The flow of gases to be delivered to the patient may be one or more of: air, a mixture of air and supplementary gas, a gas and supplementary gas.

The supplementary gas may be diverted into a reservoir during a patient's expiration phase.

The supplementary gas diverted into the reservoir during a patient's expiration phase, or at least a portion thereof, may be provided for inclusion in the flow of gases to be delivered to the patient during a patient's inspiration phase.

A flow generator may be activated to provide for a flow of the supplementary gas from the reservoir for inclusion in the flow of gases to be delivered to the patient during a patient's inspiration phase, and the flow generator may be deactivated to reduce or stop a flow of supplementary gas from the reservoir from being included in the flow of gases to be delivered to the patient during a patient's expiration phase.

The flow of gases to be delivered to the patient may be above the patient's inspiratory demand, such as above the patient's PEAK inspiratory flow (PIF) demand.

The flow of gas delivered to the patient may be varied according to the patient's breathing phase and/or according to another patient parameter.

The flow of gas delivered to the patient may be kept or maintained at a substantially constant throughout to the patient's different breathing phases and/or according to another patient parameter.

The flow of gases delivered to the patient during a patient's inspiration phase may be greater than about 40 litres/min and during a patient's expiration phase is below about 35 litres/min.

The flow of gases to be delivered to the patient may be greater than about 60 litres/min throughout different phases of a patient's breathing phases.

The flow of gases to be delivered to the patient during a patient's inspiration phase may comprise greater than about 80% supplementary gas (optionally oxygen) as an amount of the total gas delivered to the patient.

The flow of gases to be delivered to the patient during a patient's expiration phase may comprise less than about 20% supplementary gas (optionally oxygen) as an amount of the total gas delivered to the patient.

The supplementary gas is delivered as a bolus during a patient's inspiration phase.

The supplementary gas may be diverted or directed into a reservoir during a patient's expiration phase, and the supplementary gas may be provided for inclusion in the flow of gases to be delivered to the patient during a patient's inspiration phase.

The flow of gases to be delivered to the patient may be greater than about 60 litres/min during a patient's expiration to promote a lung recruitment.

The flow of gases to be delivered to the patient during a patient's expiration phase may comprise less than about 100% and greater than about 90% supplementary gas by concentration of the total gas delivered to the patient, and during a patient's inspiration phase may comprise less than about 30% and greater than about 0% supplementary gas by concentration of the total gas delivered to the patient.

The method may comprise delivering a higher than normal gas flow rate to the patient for a set period and then reduce the gas flow rate to a normal treatment level.

The method may comprise providing a range of elevated gas flow rates to the patient and then reducing the gas flow rates to a normal treatment level before it is increased to a higher gas flow rate again.

In accordance with an eighteenth embodiment disclosed herein, there is provided a an apparatus or system for controlling gases delivery to a patient via a patient interface, the apparatus or system comprising:
- a controller that receives input relating to either a patient's breathing phase and/or another patient parameter,
- a flow generator, to provide a flow of gas to be delivered to a patient,
- a flow source being a source of supplementary gas,
- a valve to control the inclusion of a supplementary gas in the flow of gas to be delivered to a patient,
- wherein the controller controls the valve, such that the amount of supplementary gas provided to the patient is substantially synchronized with respect to the patient's breathing phase and/or another patient parameter.

The controller may control the flow generator, to control the flow of gases to be delivered to a patient.

The controller may control the valve such that the patient may receive a lesser amount of said supplementary gas during an expiration phase of the patient's breathing phase relative to an inspiration phase of the patient's breathing phase.

The controller may control the valve such that the patient may receive a greater amount of said supplementary gas during an inspiration phase of the patient's breathing phase relative to an expiration phase of the patient's breathing phase.

A patient's breathing phase may be determined by a measured indicator of a patient's breathing phase, optionally the indicator is one or more of: a pressure in an airway of the patient, a patient's chest movement, a CO2 measurement in or near an airway of the patient, oxygen saturation, sensors for detecting patient breathing.

The supplementary gas may be one or more of: oxygen, helium and oxygen (heliox), anaesthetics, analgesics, nitric oxide, nitrous oxide.

The controller may receive input relating to another patient parameter, said another patient parameter comprising a measurable attribute of a patient.

The valve may be actuated to allow a supply of the supplementary gas during an inspiration phase of the patient's breathing phase.

The controller may control the flow generator and/or the valve such that the flow of gases to be delivered to the patient may be maintained at a substantially constant flow rate throughout different phases of a patient's breathing phases.

The controller may control the flow generator and/or the valve such that the flow of gas to be delivered to the patient may be substantially synchronized with a patient's breathing phase or another patient parameter.

The controller may control the flow generator and/or the valve such that the flow of gases to be delivered to the patient may be of a greater flow rate during a patient's inspiration phase and a relatively lower flow rate during a patient's expiration phase.

The flow of gases to be delivered to the patient may be one or more of: air, a mixture of air and supplementary gas, a gas and supplementary gas.

The supplementary gas may be diverted into a reservoir during a patient's expiration phase.

A second valve may be provided between the patient interface and the reservoir, the controller may control the valve such that the supplementary gas diverted into the reservoir during a patient's expiration phase, or at least a portion thereof, may be provided for inclusion in the flow of gases to be delivered to the patient during a patient's inspiration phase.

The controller may activate the flow generator to provide for a flow of the supplementary gas from the reservoir for inclusion in the flow of gases to be delivered to the patient during a patient's inspiration phase, and the flow generator may be deactivated to reduce or stop a flow of supplementary gas from the reservoir from being included in the flow of gases to be delivered to the patient during a patient's expiration phase.

The controller may control the flow generator and/or at least one valve such that the flow of gases to be delivered to the patient may be above the patient's inspiratory demand, such as above the patient's PEAK inspiratory flow (PIF) demand.

The controller may control the flow generator and/or at least one valve such that the flow of gas delivered to the patient may be varied according to the patient's breathing phase and/or according to another patient parameter.

The controller may control the flow generator and/or at least one valve such that the flow of gas delivered to the patient may be kept or maintained at a substantially constant throughout to the patient's different breathing phases and/or according to another patient parameter.

The controller may control the flow generator and/or at least one valve such that the flow of gases delivered to the patient during a patient's inspiration phase may be greater than about 40 litres/min and during a patient's expiration phase is below about 35 litres/min.

The controller may control the flow generator and/or at least one valve such that the flow of gases to be delivered to the patient may be greater than about 60 litres/min throughout different phases of a patient's breathing phases.

The controller may control the flow generator and/or at least one valve such that the flow of gases to be delivered to the patient during a patient's inspiration phase may comprise greater than about 80% supplementary gas (optionally oxygen) as an amount of the total gas delivered to the patient.

The controller may control the flow generator and/or at least one valve such that the flow of gases to be delivered to the patient during a patient's expiration phase may comprise less than about 20% supplementary gas (optionally oxygen) as an amount of the total gas delivered to the patient.

The controller may control at least one valve so that the supplementary gas is delivered as a bolus during a patient's inspiration phase.

The supplementary gas may be diverted or directed into a reservoir during a patient's expiration phase, and the supplementary gas may be provided for inclusion in the flow of gases to be delivered to the patient during a patient's inspiration phase.

The controller may control the flow generator and/or at least one valve such that the flow of gases to be delivered to the patient may be greater than about 60 litres/min during a patient's expiration to promote a lung recruitment.

The controller may control the flow generator and/or at least one valve such that the flow of gases to be delivered to the patient during a patient's expiration phase may comprise less than about 100% and greater than about 90% supplementary gas by concentration of the total gas delivered to the patient, and during a patient's inspiration phase may comprise less than about 30% and greater than about 0% supplementary gas by concentration of the total gas delivered to the patient.

The controller may control the flow generator and/or at least one valve such that a higher than normal gas flow rate is delivered to the patient for a set period and then the gas flow rate may be reduced to a normal treatment level.

The controller may control the flow generator and/or at least one valve such that a range of elevated gas flow rates is provided to the patient and then the gas flow rates may be reduced to a normal treatment level before it is increased to a higher gas flow rate again.

According to the various aspects and embodiments described herein, the methods and/or associated apparatus or systems may have particular application in:

during the transportation of a patient. During transportation (e.g. ambulance or helicopter or plane or other transport systems), the supply of medical gases, such as supplementary gases (e.g. including, but not limited to, oxygen) may be of a finite resource, and therefore the ability to provide for a conservation of those gases has particular benefits. In this manner, the finite resource can be preserved for longer use with the patient, which may be useful in situations where journeys take longer than anticipated or planned, or for other reasons, including extending the ability of the gas supply to be used for patients before needing replenishment; or for example during medical procedures where a finite source of the supplementary gas is available (for example may be during sedation of a patient or an endoscopic procedure and the gas is provided from a bottle source).

reducing or minimising potentially unnecessary delivery of gases, such as supplementary gases into an environment (e.g. a surgical theatre). This has benefits in that equipment or people in the surrounding environment may have reduced or less exposure to the supplementary gases being delivered to the patient (e.g. a surgeon or other medical assistants are not exposed to increased levels of supplementary gases, such as oxygen or anaesthetic gases);

economic considerations in that the provision of supplementary gases have a financial impact (e.g. medical grade oxygen and heliox or anaesthetic gases are relatively expensive), as such the same effective therapy can be delivered to the patient but with a reduction in the volumes used of such gases used compared to existing techniques which provide for a continuous supply of such supplementary gases, regardless of a patient's breathing phase or another patient parameter.

where the supplementary gas supply is from a finite resource (or source), and therefore the ability to provide for a conservation of those gases has particular benefits. In this manner, the finite resource (e.g. a gas bottle) can be preserved for longer use with the patient, which may be useful in situations where transport journeys or medical procedures take longer than anticipated or planned, or for other reasons, including extending the ability of the gas supply to be used for patients before needing replenishment;

for the more effective provision of supplementary gas to a patient, yet still providing for effective respiratory support of the patient. In such an instance, as per at least one of the methods or apparatus/systems as described herein allow for at least a first respiratory support mode and at least a second respiratory support mode. The first mode providing for a relatively normal mode of operation or a high flow mode where a first level of gases is to be delivered to the patient which has an inclusion of supplementary gas, this first mode can be configured to be provided according to a patient's breathing phase (e.g. during an inspiration phase) or according to another patient parameter. The second mode in which a second level of gases is to be delivered to the patient, with a reduction in the amount of supplementary gas in this flow of gases delivered to the patient, optionally the flow rate delivered to the user may be the same or constant as the first level of gases or may be reduced from that first level according to a patient's breathing phase (e.g. during an expiration phase) or according to another patient parameter.

According to the various aspects and embodiments described herein, a patient's breathing phase or another patient parameter may be by a measurement of chest movement (e.g. EIT bands) or oxygen saturation (e.g. using pulse oximetry) or pressure in an airway of the patient or a CO2 measurement in or near an airway of the patient, or other sensors for detecting patient breathing (such as electrical sensors which may be inserted down the oesophagus, at least one of which is known as a 'Nava probe' as used in the industry).

According to the various aspects and embodiments described herein, there may be provided a flow source (e.g. an air source) and a finite supply of supplementary gases (e.g. an oxygen source). A controller may be used to reduce or minimise or stop the supply of the supplementary gas from being delivered to the patient, or may reduce the amount of the supplementary gas being delivered to the patient. In this manner, the supplementary gas may be preserved or conserved. The flow source for the supplementary gases may be a relatively low flow source.

As relatively high gas delivery flow rates may be used with the embodiments or configurations described herein, the gases being supplied or delivered to the user or patient can may be delivered to different parts of the user's or a patient's airway.

For example, according to those various embodiments and configurations described herein, a flow rate of gases supplied or provided to an interface or via a system, such as through a flow path, may comprise, but is not limited to, a flow rate of between about 5 or 10 LPM and about 100 LPM, or between about 15 LPM and about 95 LPM, or between about 20 LPM and about 90 LPM, or between about 25 LPM and about 85 LPM, or between about 30 LPM and about 80 LPM, or between about 35 LPM and about 75 LPM, or between about 40 LPM and about 70 LPM, or between about 45 LPM and about 65 LPM, or between about 50 LPM and about 60 LPM. For example, according to those various embodiments and configurations described herein, a flow rate of gases supplied or provided to an interface or via a system, such as through a flowpath, may comprise, but is not limited to, flows of at least about 5, 10, 20, 30, 40, 50, 60, 70, 80, 90, 100, 110, 120, 130, 140, 150 L/min, or more, and useful ranges may be selected between any of these values (for example, about 40 to about 80, about 50 to about 80, about 60 to about 80, about 70 to about 100 L/min, about 70 to 80 L/min).

Such relatively high flow rates of gases may assist in providing the supplied gases into a user's airway, or to different parts of a user's airway, for example such flow rates may allow for a delivery of such gases to the upper or lower airway regions. Upper airway region typically includes the nasal cavity, pharynx and larynx, while the lower airway region typically includes the trachea, primary bronchi and lungs.

Each of the various configurations or embodiments or configurations described herein may be utilised in combination with one or more of the other various systems, devices (including interfaces) or methods also described herein.

The term "amount" as used in this specification means an amount of the supplementary gas on the basis of at least:
  a concentration fraction of the supplementary gas as a component of the total gases components delivered to the patient,
  a volume fraction of the supplementary gas as a component of the total volume of gases delivered to the patient,
  a flow rate fraction of the supplementary gas as a component of the total gas flow rate delivered to the patient,
  a mass flow rate fraction of the supplementary gas as a component of the total gases mass flow rate delivered to the patient.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

The invention consists in the foregoing and also envisages constructions of which the following gives examples only.

BRIEF DESCRIPTION OF THE DRAWINGS

Preferred embodiments of the invention will be described by way of example only and with reference to the drawings, in which.

DETAILED DESCRIPTION OF SPECIFIC EMBODIMENTS

Oxygen and/or other gases can be provided to a patient using a high flow apparatus/source. The supplies of such gases may come from a source of limited capacity, or there may be other drivers for avoiding the unnecessary use or depletion of those gases. Therefore, systems for better utilisation of the supplied gases would provide for particular advantage.

Lung recruitment involves maintaining a pressure to ensure the alveoli remain open.

Atelectasis is a condition where there is a collapse of a part or all of a lung which commonly occurs under anaesthesia and post-extubation. Once atelectasis has occurred the pressure required to re-open the collapsed alveoli is much greater. This higher or greater pressure can potentially cause barotrauma to the already open alveoli and the re-opening process can cause tissue trauma to those alveoli which had collapsed.

Figure 7:
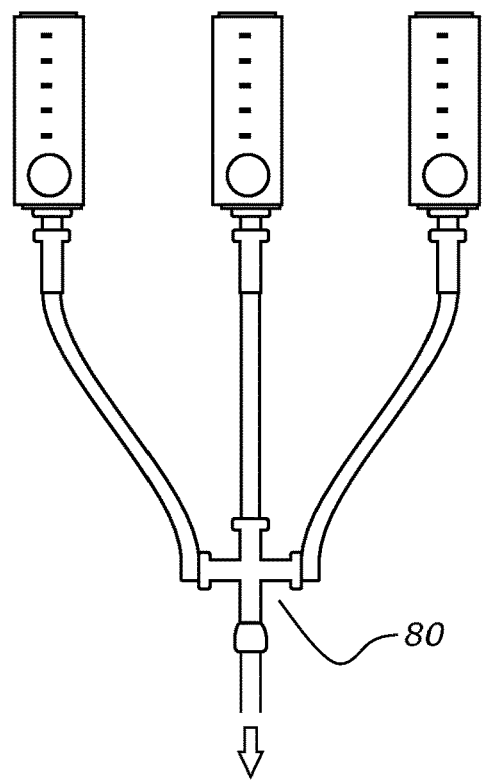
FIG. 7 illustrates three flow sources coupled via a Y-piece.

On anaesthesia machines there can be two to three independent flow control devices (comprising flow meters and flow control mechanisms, such as valves), such as shown in FIG. 7 for coupling to an oxygen flow source (more generally "gas flow source" or "flow source").

The flow control devices are typically controllable to control the oxygen flow from the flow source.

The flow source itself might comprise one or two or three or even more separate flow sources (such as oxygen tanks or in-wall oxygen supplies and even more generally a flow generator), each coupled to a flow control device, again, as for example shown in FIG. 7.

The term "flow source" can therefore refer to individual flow sources, or more generally the combination of several flow sources. Each flow control device typically has a maximum flow rate, for example of 15 L/min of 100% oxygen.

Nasal high flow (utilising, for example, a high flow therapy apparatus) may be used to increase oxygen saturation of a patient, for example when a patient is spontaneously breathing, or non-spontaneously breathing. In these scenarios, a spontaneously breathing patient may for example be breathing on their own accord, such as in the instance of prior to a patient being anaesthetised and needing to undergo an intubation procedure (e.g. the patient is spontaneously breathing of their own accord); or for a patient who has a diminished respiratory drive (e.g. patient who is ill or obsess patients or patients who may have been sedated and as a result their lungs or respiratory system is not working at full capacity).

With the advent of nasal high flow, and its intended use in the anaesthesia setting, it is conceivable the maximum oxygen flow rate demand (e.g. 70 L/min of 100% oxygen) would exceed the maximum oxygen flow rate capability of the flow control device (e.g. 15 L/min). Hospitals, for example, could switch using the flow control devices with a higher maximum flow rate capacity to meet a higher flow rate demand—however, for various reasons this switching may still not make the provision of the required gas flow (e.g. 70 L/min) possible.

The following embodiments relate to allowing nasal high flow to be typically used with a limited supply of oxygen or limited supply of other medical gases or where it is desired to conserve such oxygen and/or those other medical gases which are otherwise to be supplied to the patient.

The embodiments described provide arrangements that assist with management/control of usage of oxygen supply, or supply of other medical gases, to reduce or prevent depletion or supply of such gases at stages when it is unnecessary (e.g. during the expiration phase of a patient's breathing phase) or not desired (e.g. if there is another reason why the supply of such gases to the patient at a particular time is not wanted, such as, but not limited to, supplying gases which contribute to a flammable situation, such as oxygen, when an ignition source is in operation, such as but not limited to, a cauterising laser).

While the embodiments are described in relation to nasal high flow in relation to anaesthesia, it should be noted these embodiments are not exclusive to anaesthesia. It is conceivable the embodiments could also be used with other medical gases (e.g. air, nitrogen, carbon dioxide, medical gas mixtures including medical gas analgesics, such mixtures including for example: heliox (a mixture of helium and oxygen), nitric oxide, nitrous oxide (a mixture of nitrogen and oxygen)) needed and/or in a general respiratory setting to allow for a limited supply to be used with nasal high flow.

The following embodiments can utilise the knowledge of the respiratory flow wave and/or the transition between inspiration and expiration. For example patent applications U.S. 61/94,800, U.S. 62/611,221, U.S. 62/036,769, and U.S. 62/046,000 refer to possible methods and apparatus for respiratory flow wave, meeting (e.g. peak) inspiratory demand and estimating (e.g. peak) inspiratory demand and are incorporated herein in their entirety.

It should also be noted that the following can utilise switching modes of operation based on a patient's breathing phases of inspiration and expiration and/or in relation to another patient parameter. For example, the controller can operate to switch the controlled valve between a first configuration and a second configuration to either i) direct a flow of gases otherwise being supplied to a patient to a reservoir or storage facility, such as during a patient's expiration phase or in relation to another patient parameter, or ii) direction the flow of gases to a patient interface for delivery to the patient, such as during a patient's inspiration phase or in relation to another patient parameter) The exact moment of switching does not need be limited to match or be synchronised with the exact transition point between a patient's breathing phases, although it may be helpful. Similarly, switching modes of operation does not need to be limited to matching or being synchronised with the patient's breathing phases and may instead be synchronised with another patient parameter.

According to the various embodiments as described herein, a respiratory support system can be provided that facilitates for respiratory support of a patient. A manually activated control or switch can be enable to then allow the system to switch over to an automated mode which then facilitates the flow of gases to be delivered to the patient to be controlled according to the patient's breathing phases or by another patient parameter.

The other patient parameters may comprise one or more of at least the following:
whether a source of ignition is detected as being put into operation or has been triggered to turn on for operation (e.g. a laser), in which case the controller can control the valve to direct the supply of gases which may otherwise contribute to the hazard or increase the risk of an ignition to the reservoir or storage facility so as to be stopped from supplying such gases to the patient interface;
whether a source of ignition is detected as being taken out of operation or has been triggered to turn off from operation, in which case the controller can control the valve to direct the supply of gases which may otherwise contribute to the hazard or increase the risk of an ignition back to the patient interface (optionally some of these gases may be provided to a breathing circuit for delivery to the patient interface from the reservoir or storage facility);
whether a particular device has been detected as being put into, or taken out of, operation for a procedure to be associated with the patient;
whether a particular device has been triggered to turn on, or turn off, for a procedure to be associated with the patient.

Figure 1A:
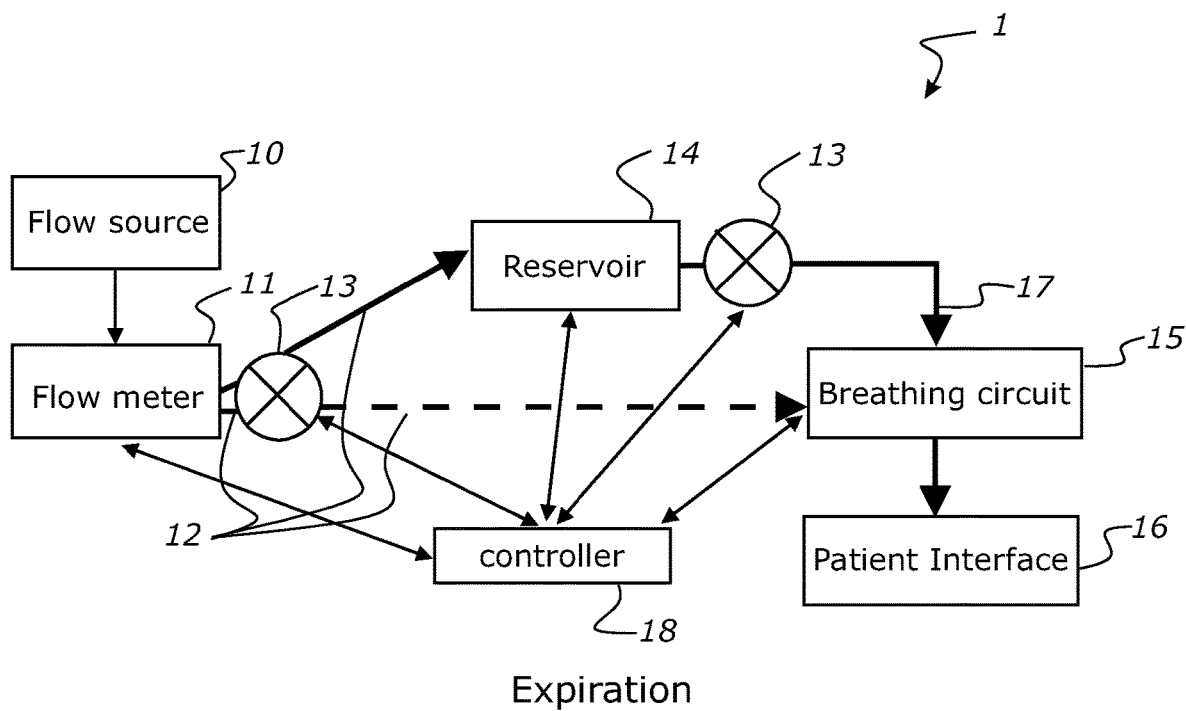
FIGS. 1A, 1B illustrate expiration and inspiration configurations respectively of a system to control supplementary gas delivery to a patient.
Figure 1B:
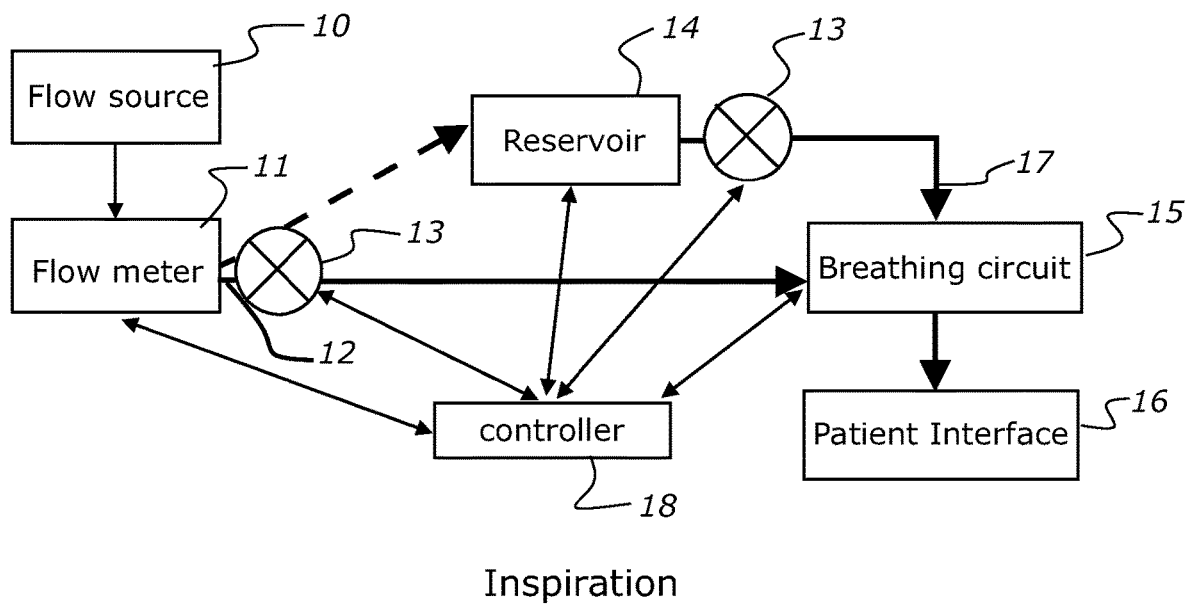

FIGS. 1A and 1B show two configurations (for expiration and inspiration) of an apparatus/system 1 that is or comprises a high flow apparatus (such as nasal high flow), and is configured to control delivery of a gas from a flow source 10 (e.g. an oxygen source) during expiration and inspiration phases of a patient, in accordance with a first general embodiment.

The configurations of FIGS. 1A, 1B can be used to ensure sufficient delivery of desired gases to a patient during anaesthesia or other situations as described above, for example this may comprise assisting with oxygenation of a patient where oxygen is supplied via the flow source 10. However, it will be appreciated that where multiple gases are to be supplied to the patient, these may come from multiple flow sources (other such flow sources not shown, but would be provided upstream of valve 13 that is controlled as to its operation by controller 18). In this embodiment there can be a storing of oxygen or the other gases supplied from the different flow sources, such as into the reservoir 14 (it will be appreciated, each such flow course may be associated with its own separate valve (such as valve 13) and its own separate reservoir (such as reservoir 14). In this manner, the preservation of each of the supplied gases can be achieved. For example, during a patient's breathing phase of expiration, the gases from the various sources can be directed to their associated reservoirs or storage facilities, whilst during a patient's breathing phase of inspiration, the gases from the various sources can be directed to the breathing circuit 15 for delivery to patient interface 16. The gases may be oxygen or any one or more of the gases previously described herein, or may be other gases as may be used for a patient via a breathing circuit.

In prior art systems, flow delivered to a patient during expiration provides respiratory support (e.g. pressure and flushing of the nasal cavity). However, the majority of this delivered flow is expelled back into the atmosphere and is not used by the patient (i.e. the pressure may be useful for effectively splinting open an airway only, but the supplied gas is otherwise not used by the patient). The oxygen from this flow is not absorbed by the patient, as the patient expels majority of the flow delivered during expiration.

Therefore, in situations with a limited flow rate supply (or even a limited supply of a gas), it may be deemed more important to deliver high flows of gases (such as oxygen or other gases previously described) to a patient during an inspiration phase when such gases are more likely to be utilised or absorbed by the patient, for example entering the lungs, in contrast to providing a flow of gas to support an airway during an expiration phase of the patient. Accordingly, during an expiration phase in an embodiment to be described below, gases, such as oxygen, from the flow source 10 are stored in a reservoir 14 and the patient receives no flow (or a reduced flow) of gases. Upon an inspiration phase, the reservoir 14 can be opened and the gases, such as oxygen, from the reservoir 14 can be added to the gases, such as oxygen, supplied from the flow source 10 to create an overall higher flow rate of oxygen for such an inspiration phase. The gas, such as oxygen, may be added as a bolus to the breathing circuit 15. In such an embodiment, the flow source 10 may be a source of gases of a constant flow.

In another embodiment, an additional supply of supplementary gas may not be needed in addition to the supplementary gas that has been diverted or directed to the reservoir. As such, the reservoir can provide for the whole of the necessary supplementary gas supply during a patient's inspiratory phase and the amount of supplementary gas to be provided to the flow of gas to be delivered to the patient. This may be enabled as a patient's expiration phase is generally longer than an inspiration phase. Accordingly, in this embodiment, the longer expiration phase will allow the reservoir to build a greater amount of the supplementary gas up within the reservoir. Therefore, there may be no need to have an additional supplementary gas supply from the flow source. The reservoir can provide the supplementary gas as a bolus, and may for example be released via a controllable valve from the reservoir.

Alternatively, a bolus of supplementary gas can be included in the gas flow to be delivered to the patient at the flow source via a controllable valve.

The gas (e.g. oxygen), depending on its physical properties, can be stored in the reservoir 14 or other storage facility, as a gas, or as a liquid and may optionally be aerosolised prior to being added back into the gases flow of the circuit 15, for example as a slow release, or alternatively as a jet via a jetting mechanism associated with the reservoir 14 or storage facility.

Referring to FIGS. 1A, 1B, flow source 10 could be a—wall or tank gas supply, and could comprise several flow sources as described previously. One or more flow control devices (flow meters) 11 are provided for the flow source. A gas line 12 for flow of gas (e.g. oxygen) is provided from the flow control device 11. The gas line 12 is coupled via a valve 13 from the flow control device to a reservoir 14, and placed in pneumatic connection with a breathing circuit (such as a breathing delivery conduit) 15. The breathing circuit is coupled to a patient interface 16, such as a nasal cannula or nasal mask. A gas line 17 is coupled via a valve 13 between the reservoir 14 and the breathing circuit 15. The valve could be the same or different to the valve coupled between the flow meter and reservoir and/or breathing circuit.

A controller 18 is also provided, that controls various operations of the system/apparatus 1. Among other connections, the controller is connected to the valve(s) 13 and to a portion of the system 1 that senses/monitors a patient's breathing phases and/or another patient parameter (including but not limited to: a patient's chest movements such as chest compressions using Electrical Impedance Tomography bands (referred to as EIT bands), oxygen saturation of the patient (e.g. via pulse oximeter), or patient CO2 output to provide an indicator of a patient's breathing phase or an exhalation phase of the patient, or one or more pressure sensors may be utilised (e.g. pressure sensors can be used to measure pressure in a patient airway or alternatively measure a differential pressure in the supply tube or conduit to determine the inspiration phase or expiration phase of the patient), such as the breathing circuit 15 or patient interface 16 or other sensors or monitoring devices for sensing or monitoring other patient parameters (including devices to be used upon or for a procedure associated with the patient, such as a cauterising laser or other medical devices).

The controller 18 receives input from the various sensors/monitors in the breathing circuit 15 or patient interface 16 or elsewhere so that it can monitor the patient's breathing phases or other patient parameters, and may, in particular monitor/determine, the expiration and inspiration phases and the transition between the phases of the patient.

Based on the determination of the breathing phase or other patient parameters, the controller 18 can operate to control the configuration of the valves 13.13, for example between a first configuration (to direct gas supplied from the flow source 10 to reservoir 14) and a second configuration (to direct gas supplied from the flow source 10 to the breathing circuit 15). The valve(s) can be operated to independently fluidly couple the gas line 12 between the flow source 10/flow control device 11 and the reservoir 14/breathing circuit 15, and the gas line 17 between the reservoir and breathing circuit to allow flow of gas (e.g. oxygen).

With reference for example to FIGS. 1A, B, the flow source 10 can be a source of oxygen, and may be of a relatively low flow or has a finite volume (e.g. is a gas bottle). The embodiments shown by these figures, as well as the other apparatus/system and methods as described herein provide for a source of supplementary gas (such as oxygen) which can be included in an air flow. Such an inclusion of the supplementary gas into the air flow can be controlled to be reduced or switched off entirely, for example during transport of a patient.

In more detail, FIG. 1A shows a configuration where the valve 13 is controlled to direct the supplied gas from the gas source 10 to the reservoir 14 (e.g. may be during a patient expiration breathing phase); while FIG. 1B shows the configuration during where the valve 13 is controlled to direct the supplied gas from the gas source 10 to the breathing circuit 15 (e.g. may be during a patient inspiration breathing phase); wherein dotted lines show gas lines when they are not operatively fluidly coupled. The controller 18 can also be coupled to the flow control device 11, reservoir 14 and/or any other aspect of the system 1 to receive inputs that assist with the monitoring and/or control of gas flow on the system. The flow source 10, flow control device 11 and/or reservoir 14 can be considered part of or external to the high flow apparatus.

It will be appreciated that the block diagram of FIG. 1A, FIG. 1B show functional aspects of the system/apparatus, and not necessarily the physical, or structural arrangement. Furthermore, the Figures show just one possible functional arrangement. It is possible that the valves and/or gas lines could be arranged differently. For example, the reservoir might not have a separate gas line to the flow meter, but form part of or be within the gas line to the breathing circuit and be provide with a suitable valve and/or division mechanism, or the valves may be binary valves or could be proportional valves that vary the amount of the supplemental gas (e.g. O2) delivered.

Figure 1C:
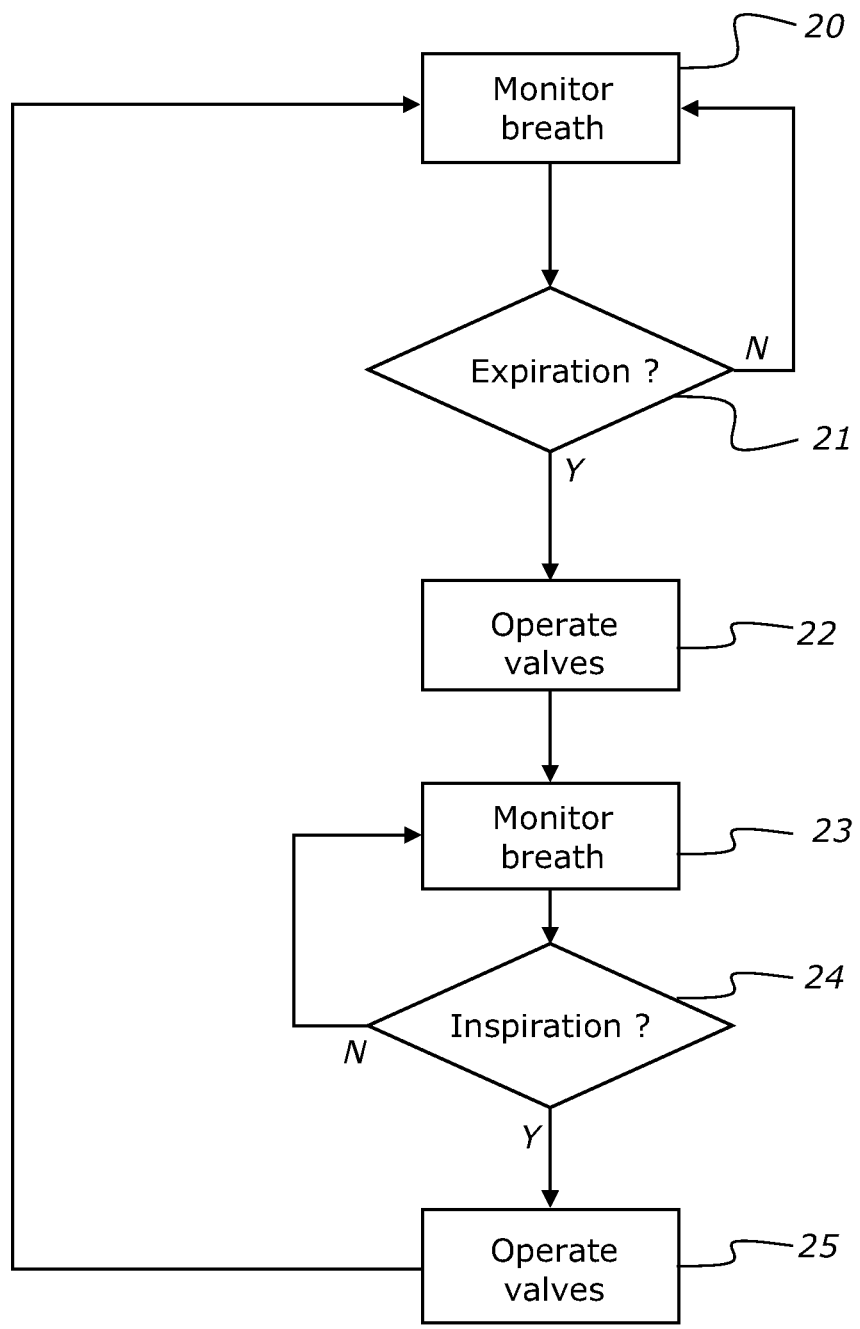
FIG. 1C shows a flow diagram of a method for controlling supplementary gas delivery to a patient.

FIG. 1C shows a method of operation of the system/apparatus in FIGS. 1A, 1B. The controller can monitor the breath flow or breathing phases of the patient, step 20. Upon detecting expiration and/or transition to expiration, step 21, the controller operates the valve(s) to fluidly close the gas line between the reservoir and the breathing circuit and/or the gas line between the flow control device and the breathing circuit, step 22. Preferably, the controller closes both, although it may be possible to close just one of the gas lines. The controller also operates the valve to fluidly open the gas line between the flow control device and the reservoir, step 22, such that the two are fluidly coupled.

During expiration, gas flows from the flow meter to the reservoir. During expiration, gas e.g. oxygen is preserved and stored in the reservoir for later delivery to the patient. Upon monitoring breath, step 23 and detecting inspiration and/or transition to inspiration, step 24, the controller operates the valve(s), step 25, to fluidly open the gas line between the reservoir and the breathing circuit and/or the gas line between the flow meter and the breathing circuit. Preferably, the controller opens both, although it may be possible to open just one of the gas lines. This fluidly couples the reservoir and/or the flow meter to the breathing circuit. The controller also operates the valve to close the gas line between the flow control device and the reservoir, step 25. During inspiration, gas e.g. oxygen is supplied to the patient in the usual way, plus the stored gas in the reservoir is supplied to the patient by way of top-up.

The method and system/apparatus enable preservation of the supplied gas (such as oxygen, but may be other gases previously described herein), while still providing the required flow rates of the gas from a gas source during inspiration. In an alternative, the method provided above can be utilised, but where the controller operates the valve(s) (e.g. at step 25) based on information or inputs other than breathing rates of inspiration and expiration, for example may be based on the detection or sensed or monitored intended operation of a medical device upon the patient (e.g. a laser may need to be used, in which case flow of flammable gases or gases which may contribute to an increased hazard or risk of ignition can be diverted to the reservoir), or may be based on detection or sensed or monitored or triggered alternative medical devices or other patient parameters to switch or divert the flow of gases from a flow source (such as a flow source 10) from being supplied to the breathing circuit 15 and patient interface 16.

It will also be appreciated that while a controller that monitors breathing phases can be utilised to control the valves, there might be passive mechanisms for redirecting flow of gas to the reservoir during expiration. Example flow controlled valves that operate based on the direction of breath flow could be utilised to redirect gas to the reservoir during expiration, and direct gas to the patient interface during inspiration. As noted above, alternatively the valves can be controlled to redirect gas to the reservoir or to direct the gas to the breathing circuit based upon other patient parameters or inputs. In a further example, a one way valve(s) configured to block or occlude the gas flow from being delivered to the interface as a patient expires may be utilised (e.g. either in a gas tube or conduit or as part of the patient interface), such a one valve operational to help reduce or prevent back flow or a pressure increase in the patient interface or a component of a breathing circuit (e.g. a gas supply tube or conduit). These various alternatives are also possible for the following embodiments.

Figure 2:
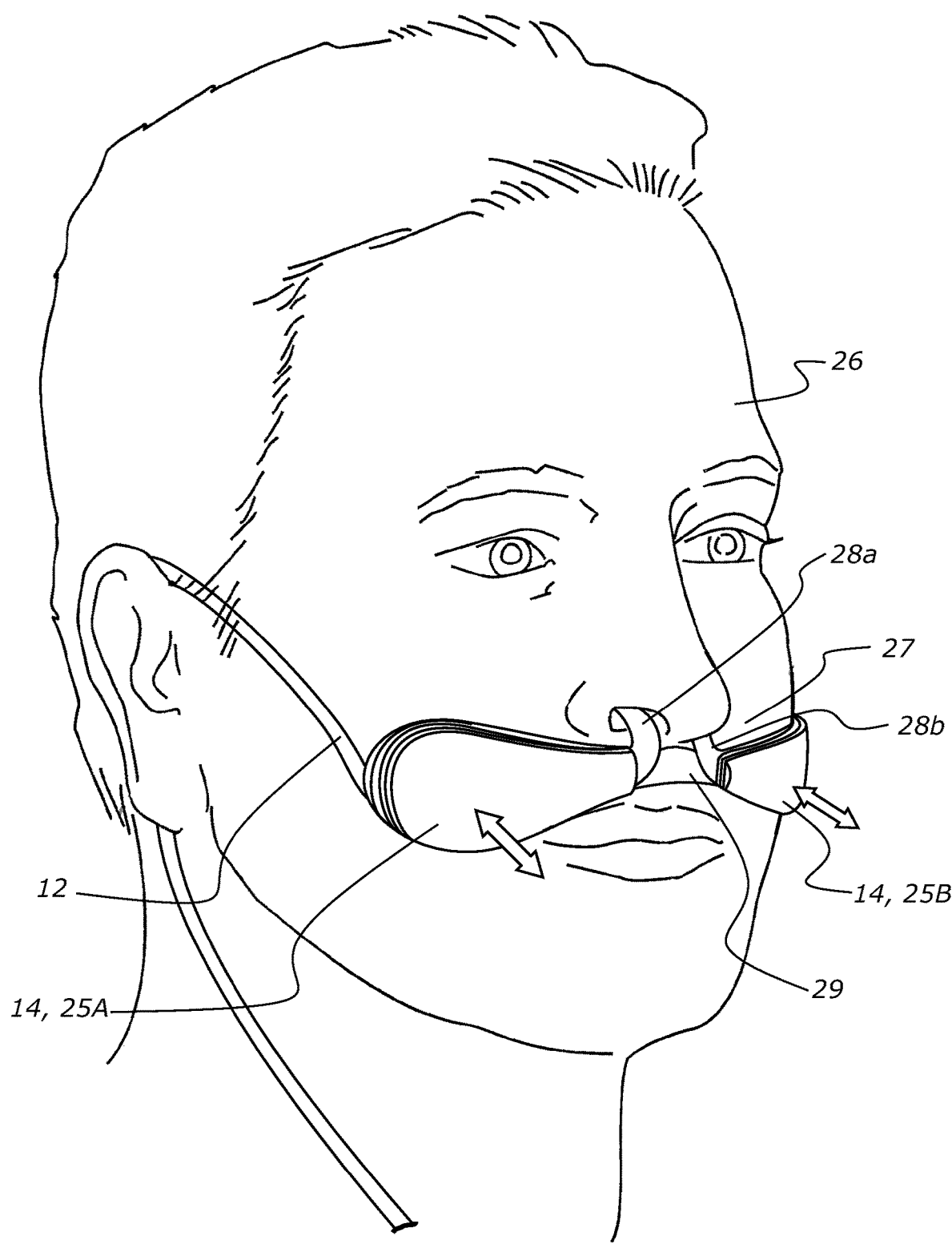
FIG. 2 illustrates a nasal cannula and supplementary gas reservoir.
Figure 3:
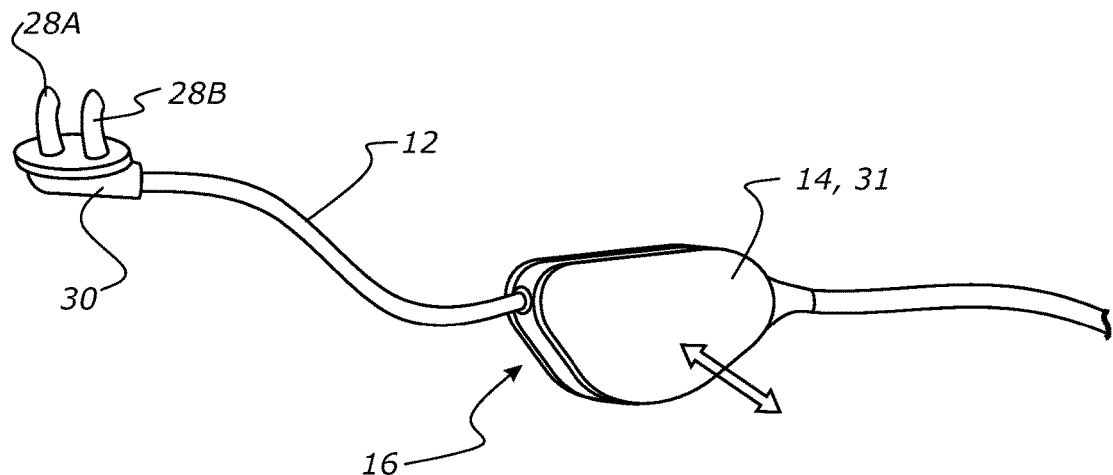
FIG. 3 illustrates a nasal cannula and a supplementary gas reservoir.
Figure 4:
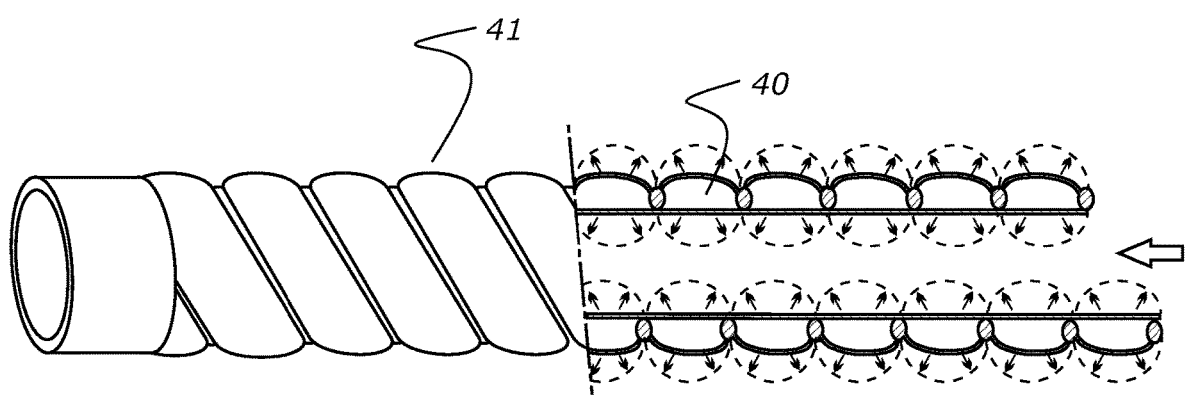
FIG. 4 illustrates a bubble tube comprising a reservoir.

FIGS. 2, 3 and 4 show three possible examples of the embodiment that is shown in FIG. 1A, 1B, including different possible reservoirs.

Examples of possible reservoirs are as follows. Note that these could be used as single reservoirs or combined for more storage:

- a patient interface that is expandable. An example is shown in FIG. —2-2 of a nasal cannula with expandable pillows on the face.
- a plastic or metal container that is separate and attached into the system. It could be made of an expandable material to increase capacity. Instead of being separate it could be built into a humidifier or connection between the breathing circuit and patient interface. FIG. 3 shows an example.
- The void spaces of a hollow bead in a tube of a breathing circuit could be formed or the walls of these voids could be made of a material that is expandable to allow for a greater volume in the tube itself (i.e. the tube has a volume that can be expanded or enlarged upon supply or storage of gas in that tube). FIG. 4 shows an example of this. In this context, there is provided a conduit for a medial breathing circuit, the conduit comprising a double-walled conduit, wherein a void space between the walls of the conduit may form a storage or reservoir (FIG. 4) volume for a supplied volume of gas. A gas supply line can be coupled to the wall of the conduit to supply O2 into the walls of the tube. The gas e.g. oxygen can be expelled from the reservoir during inspiration into the gas flow or directly into the interface.

FIG. 2 shows one example of a patient 26 with a patient interface in the form of a nasal cannula 27, a reservoir 14, and gas line 12 as generally in accordance with that shown by FIGS. 1A, 1B. The nasal cannula comprises one or more nasal prongs 28A, 28B coupled via a bridge 29 as shown, or alternatively may be coupled via a manifold that provides for a pneumatic connection of supplied gases to the patient interface (for example, a manifold may be used to provide a single source of gas to the pair of prongs). A gas line 12 originating from the flow control device 11 couples to the nasal prongs either directly, or may be via a manifold.

Forming part of the nasal cannula, or being attached to it, are one or more reservoirs 14 in the form of expandable bellows 25A, 25B, which can sit on and/or be attached to the face of the patient 26 (for example via a releasable securement system, such as of the type described by WO2012/053910, the contents of which are incorporated herein in their entirety or alternatively using a headgear such as a bifurcated headgear). The bellows are coupled to the flow control device/flow source by the gas line 12. During expiration, gas (e.g. oxygen) in the gas line 12 is directed by a valve(s) to the one or more bellows 25A, 25B, which inflate and store the gas. During inspiration, the valve(s) are operated such that the gas in the reservoir 25A, 25B is directed to the nasal prong(s) 28A, 28B. The valve(s) also close off the reservoir 25A, 25B so that it does not receive gas from the flow source, and also optionally can open the gas line between the flow source/flow control device to the breathing circuit to provide gas from the flow source.

With the detail above, as described previously, it will be noted that the directing of the gas to the reservoir or not, or the switching on and off of the gas such as supplementary gas for provision to the breathing circuit (for delivery to a patient interface) may be determined by a patient parameter other than the breathing phase of the patient, FIG. 3 shows another example with a nasal cannula patient interface, reservoir 14/31 and gas line 12. In this embodiment the nasal cannula comprises a manifold 30 with two nasal prongs 28A, 28B, and the reservoir is an expandable bellows 31 in the gas line itself, removed from the nasal cannula. Similar in operation to that described with respect to FIG. 2, during expiration, gas in the gas line is directed by a valve(s) to the bellows 31, which inflate and store the gas. During inspiration, the valve(s) are operated such that the gas stored in the reservoir 31 is directed to the nasal prong(s). The valve(s) also close off the reservoir 31 so that it does not receive gas from the flow source (e.g. flow source 10), and also optionally can open the gas line between the flow source/flow control device to the breathing circuit to provide the gas from the flow source.

FIG. 4 shows another example in which the reservoir is formed from the void spaces of a conduit having a hollow bead" 40 in a bubble tube 41 type breathing circuit. Functionally, this can operate in much the same way as shown in FIG. 1A-,-1B and also as described in relation to FIGS. 2, 3 wherein during expiration valve(s) are operated so that gas is directed to and stored in the void space or hollow bead of the tube, that void space or hollow bead then expanding, and during inspiration the valve(s) are operated to release the stored gas from the void space or hollow bead back to the patient circuit.

Figure 5A:
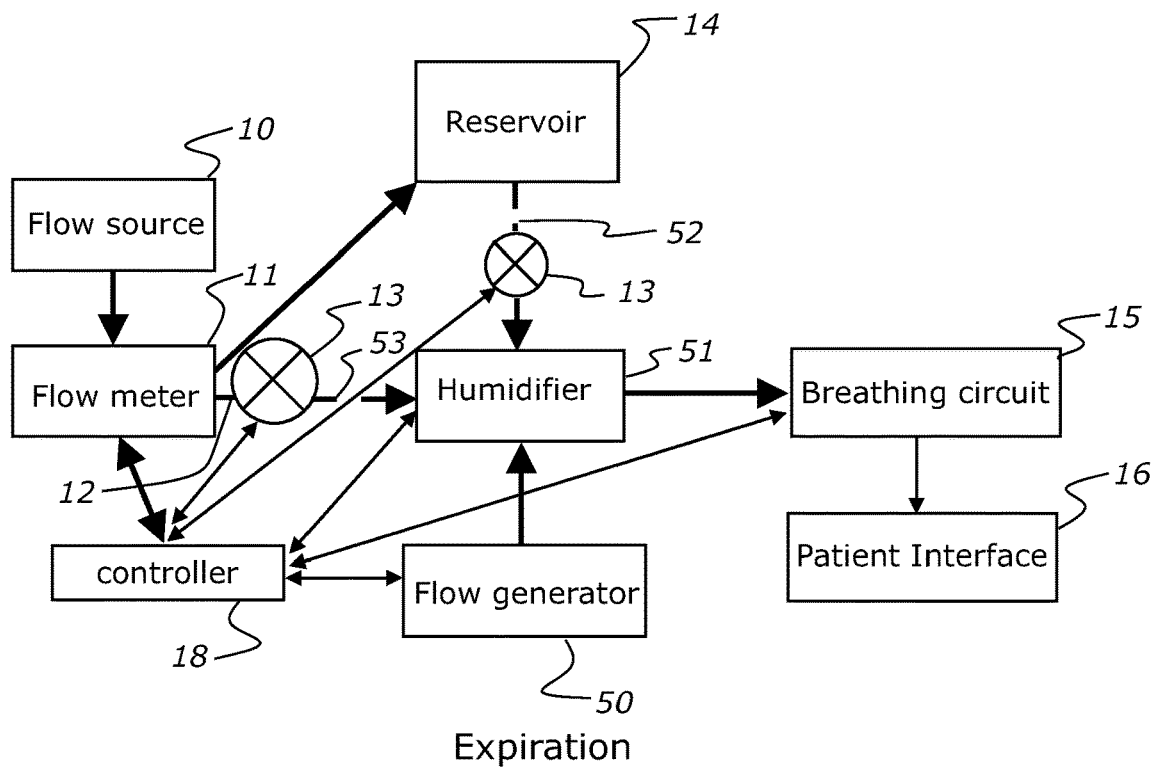
FIGS. 5A, 5B illustrate expiration and inspiration configurations respectively of a system to control supplementary gas delivery to a patient.
Figure 5B:
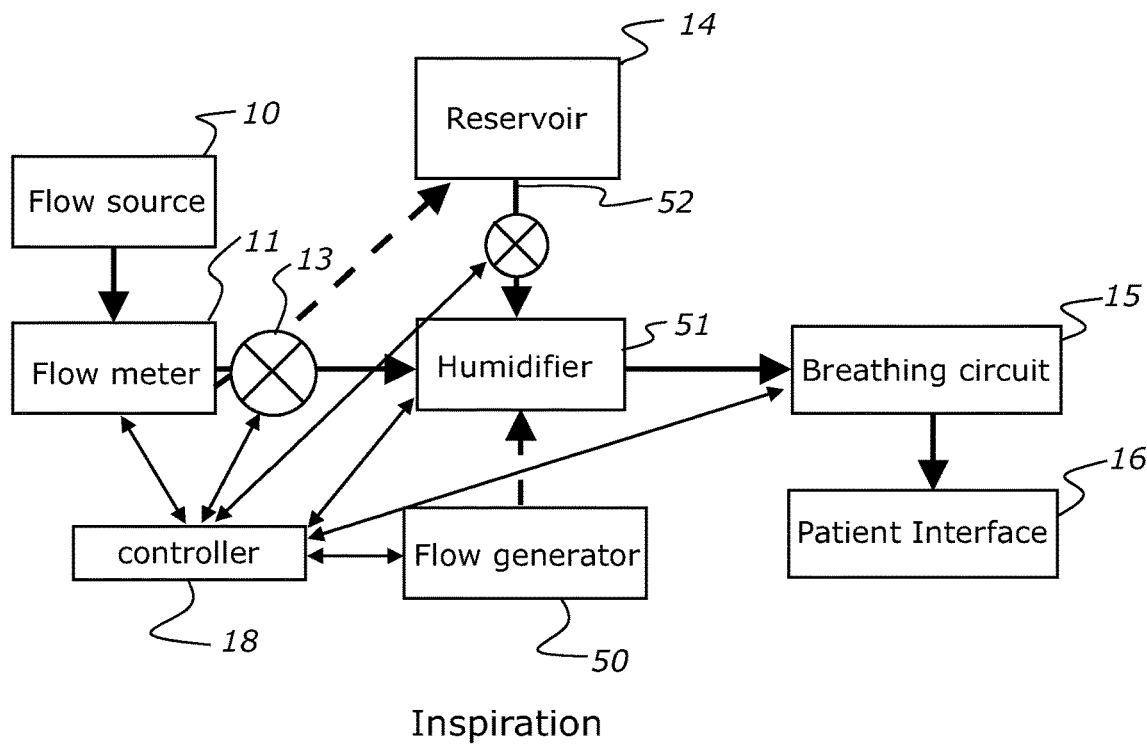

FIGS. 5A, 5B show an apparatus/system 1 that is or comprises high flow apparatus (such as nasal high flow) and is configured to control gas delivery during expiration and inhalation, or in accordance with other patent parameters, in accordance with a second general embodiment. FIG. 5A shows the configuration where the valve is controlled to be put into a first configuration (e.g. for expiration), and FIG. 5B shows the configuration where the valve is controlled to be put into a second figuration (e.g. for inspiration). This embodiment is based on an adaptation of using a high flow therapy apparatus that optionally may comprise a flow generator.

Where a flow generator is not used, the gas supply or flow source provides for its own flow (e.g. from an in-wall gas supply connection)—a valving arrangement can be provided and can be controlled to facilitate for varying the amount of gas from the flow source being included in the flow of gas to be delivered to the patient.

Figure 6:
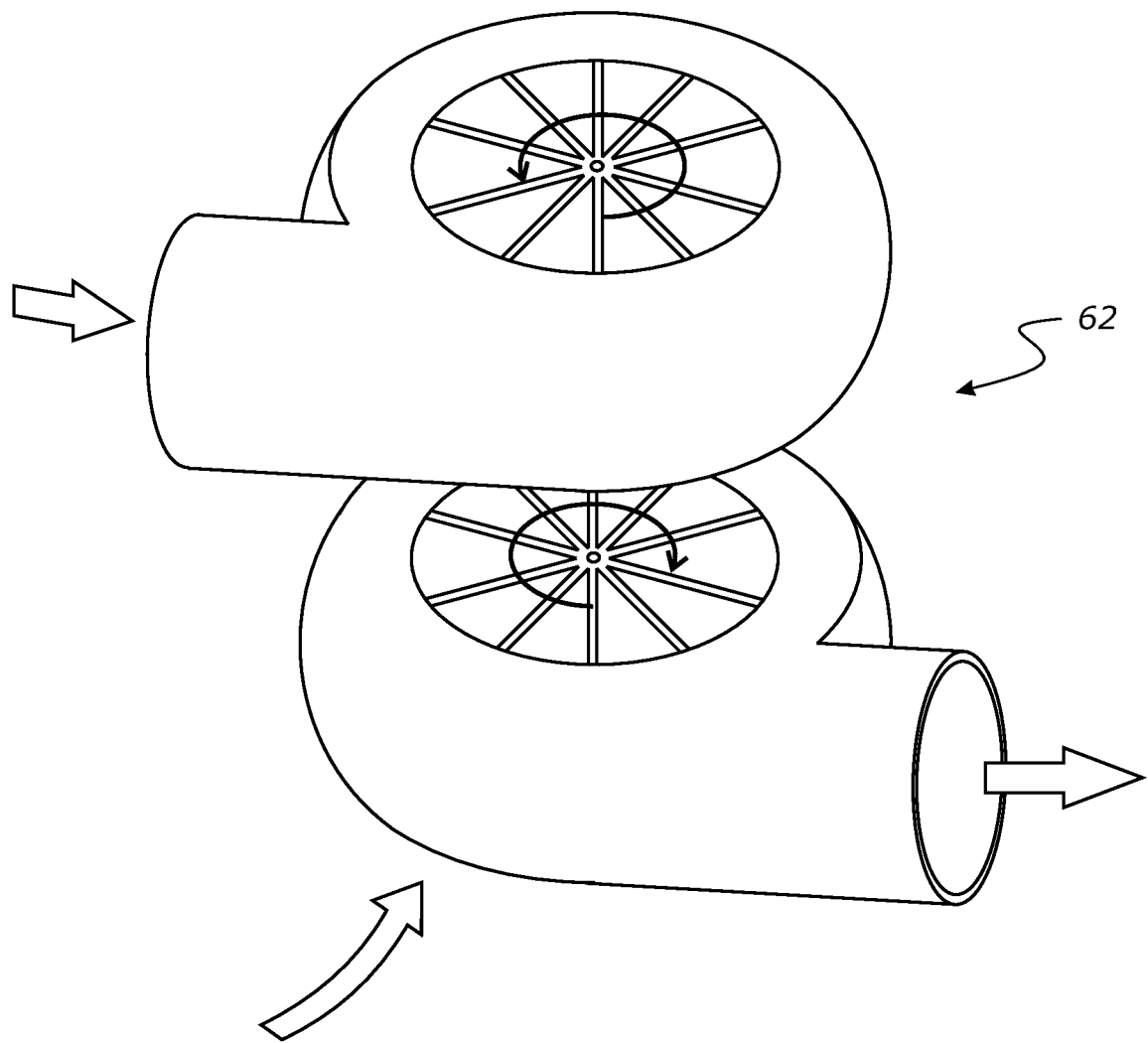
FIG. 6 is an example of a turbine that can be used in various embodiments.

It will be appreciated that a flow generator for both an air supply and a supplementary gas supply may not be needed as each source of these gases may be pressurised to then provide for their own flow. Such an apparatus generates a flow of gas (usually air, although it may be supplemented with oxygen or other gases), for example optionally using a flow generator 50, such as a blower or turbine 62 comprising a motor and impeller such as shown in FIG. 6. The gas is directed through a humidifier 51, wherein it collects humidity before being passed through a breathing circuit 15 to a patient interface 16. The optional flow generator and optional humidifier functions are controlled by a controller 18, which also monitors the breath, for example, in the breathing circuit, or can monitor other patient parameters or can control based on other inputs.

According to the above, the flow source may be provided by the flow generator (i.e. a blower or a turbine). The supplementary gas source (such as O2) can be connected to an inlet of the blower such that the blower acts as a mixer of gases (e.g. air and the supplementary gas, such as O2) from the inlet. Alternatively, the supplementary gas (e.g. O2) source may be connected to the outlet of the blower such that supplementary gas is mixed into another gas (such as an air) stream from the blower.

According to the various embodiments described herein, a gas flow (such as a high flow) (e.g. of air) can be delivered to the patient throughout the patient's inspiration and expiration breathing phases. In this manner, the provision of the gas flow as a relatively high flow can provide for particular advantages or can at least in part increase the overall O2 delivered, or may increase flushing of the patient's airways (e.g. to flush out CO2), or may provide for a reduction in the respiratory effort required by the patient. The supplementary gas may be of a type which is particularly useful for a patient when in an inhalation phase, as such O2 is one such example of a suitable gas which provides for particular patient benefits when inhaled and when such a supplemental gas is only delivered during the patient's inspiration phase to help reduce wastage of O2 or the supplemental gas.

Referring to FIGS. 5A and 5B, a flow source 10 is provided that could be a wall or tank supply (e.g. a supplementary gas for example oxygen), and could comprise several flow sources as described previously. One or more flow control devices 11 (flow meters) are provided for the flow source. A gas line 12 for flow of gas (e.g. oxygen, but could be other gases, separate or mixtures) is provided from the flow control device. The gas line is coupled via a valve 13 from the flow control device to reservoir 14. An optional flow generator 50 can be provided, that supplies a flow of gas to an optional humidifier 51, which outputs the flow of gas to a breathing circuit 15 (such as a breathing delivery conduit).

The breathing circuit is coupled to a patient interface 16, such as a nasal cannula or nasal mask. A gas line 53 is coupled from the flow meter 11 via the valve to the optional humidifier. A gas line 52 is coupled via a valve between the reservoir and the optional humidifier 51. The valve could be the same or different to the valve coupled between the flow control device and reservoir and/or optional humidifier. A controller 18 is also provided, that controls various operations of the system/apparatus.

Among other connections, the controller is connected to the valve(s) 13 and to a portion of the system 1 that senses/monitors patient breathing or other patient parameters or other inputs, such as the breathing circuit. The controller 18 receives input from sensors/monitors in the breathing circuit so that it can monitor breathing or the other patient parameters or other inputs, and in particular, but limited to, may monitor/determine expiration and inspiration phases and the transition between the phases.

Based on, for example, the determination of the breathing phase or other patient parameters or inputs as described previously herein, the controller can operate the valves.

The valve(s) can be operated to independently fluidly couple the gas line between the flow control device and reservoir and/or optional humidifier; and between the reservoir and humidifier to allow flow of gas (such as oxygen). The controller 18 can also be coupled to the flow control device 11, reservoir 14 and/or any other aspect of the system to receive inputs that assist with the monitoring and/or control of gas flow on the system. The flow source 10, flow control device 11 and/or reservoir 14 can be considered part of or external to the high flow apparatus.

It will be appreciated that the block diagram of FIGS. 5A, 5B show functional aspects of the system/apparatus, and not necessarily the physical, or structural arrangement. Furthermore, they show just one possible functional arrangement.

It is possible that the valves and/or gas lines could be arranged differently, for example. In one example, the reservoir might not have a separate gas line to the flow control device, but form part of or be within the gas line to the humidifier circuit and had a suitable valve and/or division mechanism. The various hardware items could be separate or combined together.

Figure 5C:
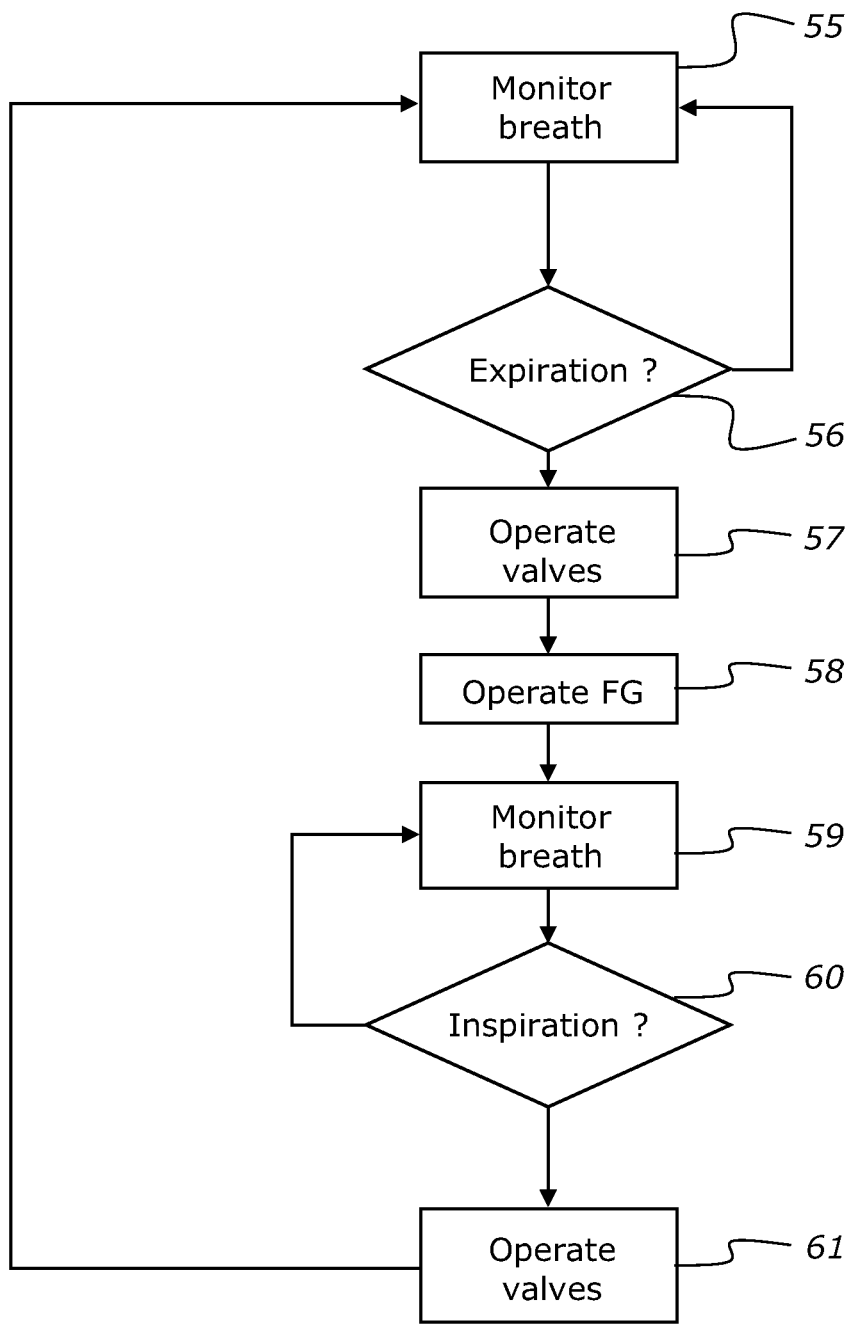
FIG. 5C shows a flow diagram of a method for controlling supplementary gas delivery to a patient

FIG. 5C shows a method of operation of the system/apparatus in FIGS. 5A, 5B. The controller 18 monitors the breath flow of the patient, step 59. During inspiration, step 60, the flow source via the flow control device operates valves to deliver gas (e.g. oxygen) to the patient via the humidifier and breathing circuit as shown in FIGS. 5A, 5B, step 61. The reservoir also delivers previously stored gas (e.g. oxygen) to the patient interface by the humidifier and breathing circuit as shown in FIGS. 5A, 5B. Flow from the flow generator to the humidifier is ceased, either by the controller turning off the flow generator, or otherwise preventing gas flow from reaching the humidifier. During inspiration, gas is supplied to the patient in the usual way, plus the stored gas in the reservoir is supplied to the patient by way of top-up.

Upon monitoring breath flow, step 55 and detecting expiration and/or transition to expiration, step 56, the controller operates the valve(s) to fluidly close the gas line between the reservoir and the humidifier circuit and the gas line between the flow control device and the humidifier, step 57. The controller also operates the valve to fluidly open the gas line between the flow meter and the reservoir, such that the two are fluidly coupled, step 57. During expiration, gas flows from the flow meter to the reservoir. During expiration, the gas (e.g. oxygen) is preserved and stored in the reservoir for later delivery to the patient. At the same time, the controller also operates the flow generator to provide a flow of gas to the humidifier and on to the patient interface by the breathing circuit, step 58. This generates air flow at a higher flow rate (e.g. 70 L per minute, or could be lower such as 30 LPM or 40 LPM depending on how much support is desired during, say, an expiratory phase of the patient) for delivery to the patient to ensure consistent therapy is continued during expiration. The method and system/apparatus enable preservation of gases, such as those described herein, while still providing the required flow rates during inspiration, and providing consistent therapy during expiration.

A flow generator may be provided for supply of air and a separate flow generate may be provided for supply of supplementary gas. Or, a single flow generator may be used to providing a flow of air and the supplementary gas to the patient. Each of these flow generators may be independently controlled so as to vary the amount of gas being supplied for delivery as the flow of gas to the patient. Valves may be incorporated as necessary in order to assist with such control.

It will be appreciated that where a single flow generator is used, such a device may incorporate an air entertainer to create or boost the air supply. In still further embodiments, the reservoir (such as a supplementary gas reservoir, e.g. for O2) can stores the supplementary gas and then delivers that gas as a bolus to the flow of gas to be delivered to the patient.

Figure 5D:
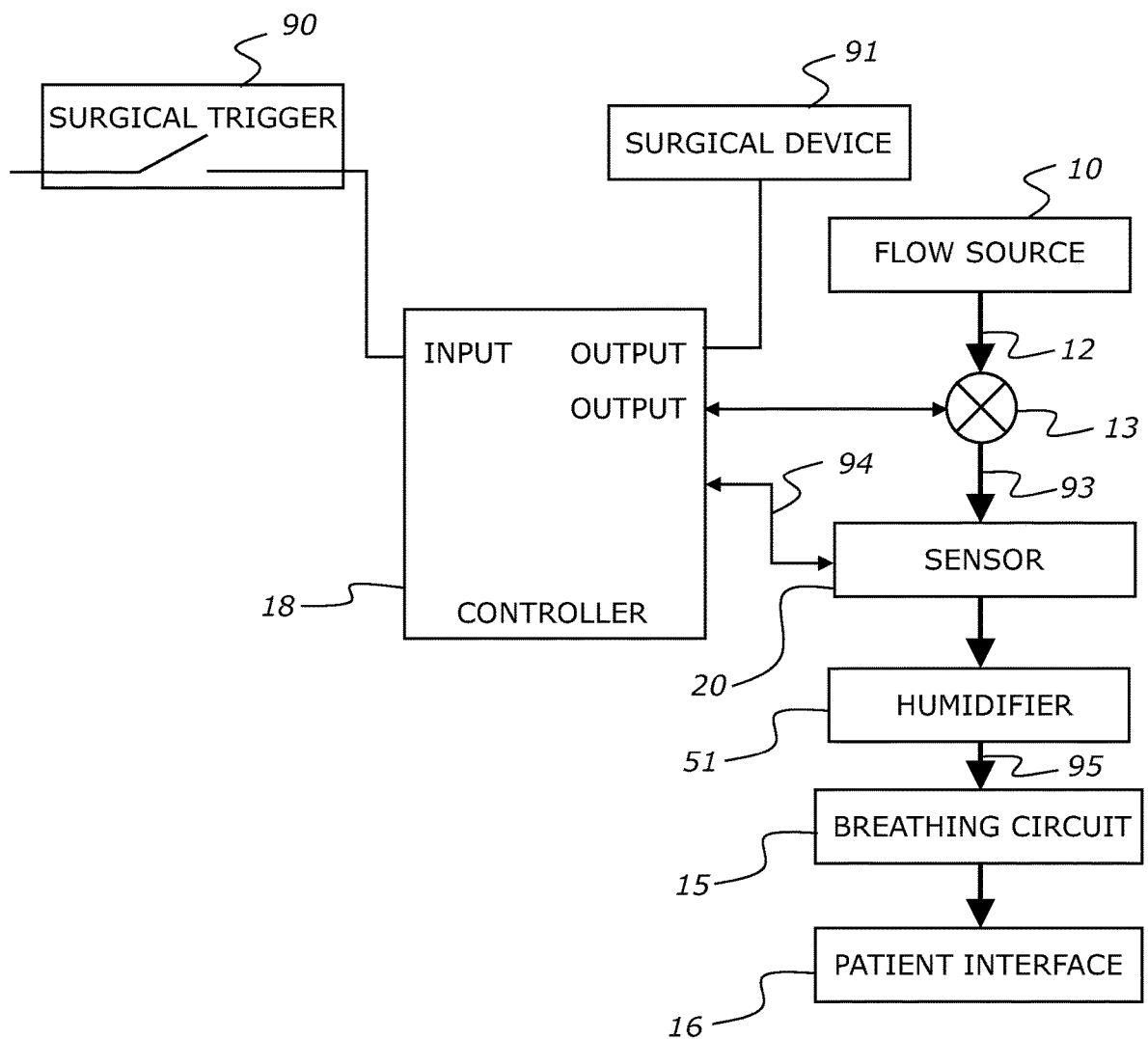
FIG. 5D shows an embodiment of a system for controlling delivery of a supplementary gas to a patient.
Figure 5E:
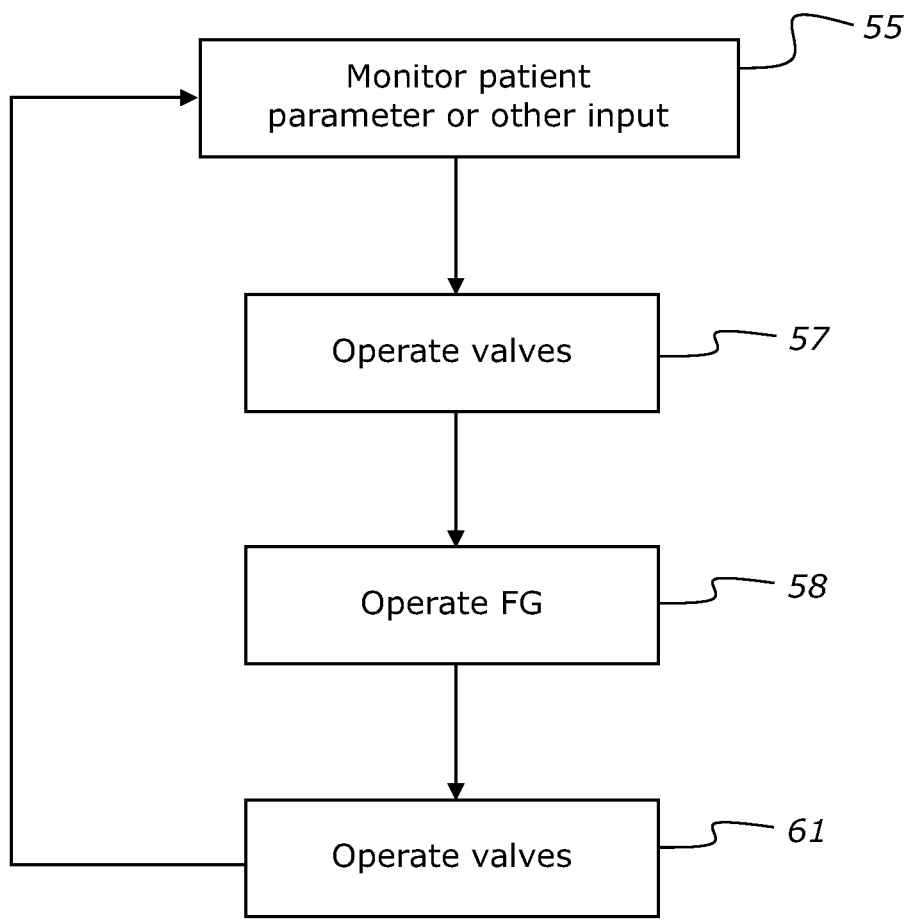
FIG. 5E shows a flow diagram of a method for controlling a system utilising valves according to the disclosure.

According to the system/apparatus as described above in relation to FIGS. 5A, 5B, an alternative is also contemplated in which the reservoir is optional. FIG. 5D illustrates an embodiment in which, due to control system, a reservoir can be avoided.

In cases where 100% oxygen is not a strict requirement or a patient is not breathing, a flow generator could be used to supplement the oxygen flow source during inspiration with additional air to make a high flow or to provide a different therapy of respiratory support (e.g. pressure support) (e.g. go from about 15 L/min 100% oxygen to about 70 L/min 38% oxygen). It will be appreciated this may be applied in situations where different gases or gas mixtures are to be used of different desired concentrations for the patient. In this way, a relatively constant flow rate of gases can be administered or delivered to the patient, yet the amount of a supplementary gas can be varied according to the patient breathing phase or according to another patient parameter.

The flowrate of gases delivered to the patient may be kept substantially constant or may be maintained at substantially the same level throughout different phases of a patient's breath phases, or there may be step changes depending on the breathing phase, such as during an inspiration or expiration phase. For example, the flow may be set to meet PEAK inspiratory demand during an inspiratory phase of the patient (e.g. 35 LPM), and reduced flow during an expiratory phase to reduce back pressure experienced by the patient during an expiratory phase.

Alternatively, the flowrate could vary during the course of a breath cycle (e.g. to meet the patient's instantaneous inspiratory demand).

The supplementary gas (such as O2) could be set substantially higher than inspiratory demand to assist with flushing out or denitrogenating the patient as fast as possible, for example during a pre-oxygenation stage of a patient being prepared or conditioned for anaesthesia, or when the patient's oxygen or other gas saturation levels are dropping.

FIG. 5D shows an apparatus/system that is configured to control the concentration and/or flow rate of gas that is provided to the patient interface. A flow source 10 is provided for supply of the gas (such as oxygen or another medical gas). A gas line 12 for flow of the gas is provided from the flow source 10. The gas line 12 is coupled to valve 13. Valve 13 is configured to control the flow or pressure of the flow of the gas, the valve may for example be a proportional valve, or another type of control valve. A further gas line 93 is provided from valve 13 to humidifier 51. Another gas line 95 is provided between the humidifier 51 and the patient interface 16

The apparatus/system comprises a controller 16. The controller 16 controls various operations of the system/apparatus. Among other connections, the controller 16 is connected to valve 13. The controller 16 operates the valve 13 to selectively allow more of less gas from flow source 10 therethrough to gas line 93, and the remainder of the system.

Optionally, a sensor 20 is located in gas line 93. The sensor measures parameters of the gas, for example an amount of the supplementary gas such as oxygen concentration or volume or mass flow rate. The sensor is connected to the controller 16 via connection 94. Connection 94 may provide power and/or receive or transmit signals to the sensor 20. The sensor 20 may be an oxygen fraction sensor which measures the fraction or percentage of oxygen in the gases (relative to other gases present) passing through conduit 93, or may measure such fractions of other gases. The sensor 20 may be located elsewhere in the system. For example the sensor 20 may be located anywhere in any of the gases lines 93, 95 the valve to the patient interface. The controller may receive a parameter from the sensor 20, related to oxygen (or other gas) fraction, concentration or percentage in the gas. Based on this parameter the controller may act to control the valve and vary the flow rate of gas through the valve.

In another embodiment, the sensor may be a flow sensor, and may be positioned between the valve 13 and flow source 10, in gas line 12. In this embodiment the amount, such as a mass flow rate of the supplementary gas, can be determined. The controller may receive a parameter from the sensor, related to the amount, for example a mass flow rate of gas. Based on this parameter (and optionally any other parameters available to the controller) the controller may act to control the valve and vary the amount, such as a flow rate of gas through the valve.

During surgery various surgical devices may be used, which comprise potential sources of ignition.

Generally, a patient is being provided with supplementary oxygen, at a concentration higher than that normally present in the atmosphere. The increased oxygen fraction of gas supplied to the patient presents an increased risk or hazard for an ignition, the ignition source for example being a medical device, such as a surgical device (e.g. a device utilising a laser). Ignition of gases can harm both a patient and those performing the procedure, where respiratory support is being provided to the patient.

A safer level, where the risk of ignition is lowered may be between about 21% and about 35% oxygen, or between about 25% and about 32% oxygen, or about 30% oxygen of the gas provided to the patient, or less.

The controller may also act to vary the flow of gas through valve 13 based on other external control signals. The system may comprise a trigger 90, connected to controller 16. The trigger 90 sends a signal to the controller 16, the signal may be related to the use, or intended use, or the enablement of a function of a surgical device 91. Surgical device 91 may for example be a cauteriser, or laser.

The trigger may be a switch (for example a foot or push button switch or other manually activated switch). A user may actuate the trigger 90 when the surgical device 91 is to be used. The controller detects the actuation of trigger 90, and acts to control valve 13. On detection of the actuation of trigger 90, the controller 16 may act to completely shut off, or restrict flow from flow source 10. The controller may reduce levels of oxygen to the safer levels within the breathing circuit such that the risk of ignition is reduced or obviated.

The controller may also control the operation of surgical device 91, or send control signals to the surgical device 91, to prevent unsafe operation. The controller may control the operation of the surgical device. The controller may be configured to supply power to the surgical device and therefore prevent the surgical device from operating. The controller may send a control signal to the surgical device corresponding to an on/off message, that lets the surgical device know when it is safe to be on. Control of the surgical device may be based on the gases data either in the breathing circuit or at the surgical site.

In this way, the switch may be manually activated by a user (as described above) or may be automatically engaged in response to a user activating (or attempting to activate) a medical device, such as a surgical device. IN this way, the switch may be directed activated a by a user or may be indirectly activated in response to a signal detected by a user attempting to operate a medical device, such as a surgical device.

Control of the surgical device 91 may be based on the concentration of oxygen in the gases of the breathing circuit, or concentration of other gases. If the concentration of oxygen or other flammable gases is within a safe region or band, or below a certain safe value then the controller 16 can provide power to the surgical device 91, and/or send a control signal to the surgical device 91 instructing the surgical device 91 to turn on. If the concentration of oxygen or other flammable gas is above a safe value, or outside of a safe band or region the controller 16 may halt the supply of power to the surgical device 91 and/or send a control signal to the surgical device 91 instructing the surgical device to turn off. Such safe levels, bands or regions may be stored in the memory of the controller 16 or may be manually set by a clinician based. Additionally, such safe levels may also be dependent on characteristics of the surgical device 91.

Alternatively, or additionally, control of the surgical device 91 may be based on the concentration of oxygen or other gases in the gases the system may also comprise an oxygen or other gases concentration sensor located near the surgical site. The oxygen or other gases concentration sensor is connected to the controller, the controller can read sensor information from the sensor. The controller may control the surgical device 91 based on the concentration of oxygen or other gases at the surgical site.

Alternatively, or additionally, control of specific functions, or parameters of the surgical device 91 may be based on gases data relating to the composition of gases in the breathing circuit (or at the surgical site). The gases data may comprise information relating to the oxygen or other gases concentration, or an oxygen or other gases fraction of the gas. The temperature of the ignition source may be controlled relative to the composition of the gases.

The gases data may be used by the surgical device or the controller to control the function, or parameters of operation of the surgical device 91 to minimise the chance of ignition of gases. For example the surgical device 91 may control the temperature of the ignition source to be below a certain temperature, or to be pulsed or controlled in a manner to reduce the potential of ignition.

The gases data may also be used by the controller 16 to control functions or parameters of operation of the surgical device directly. For example the controller may calculate suitable temperature profiles or control schemes for the surgical device 91 for particular gases data so that the risk of ignition is reduced.

Alternatively, or additionally, once the trigger 90 is activated the controller may provide for a time delay, corresponding to when the surgical device will be safe to use. Once the trigger 90 has been activated the time delay begins. After the time delay has expired the controller may act to control the surgical device as described above. The time delay may correspond to a time where the oxygen concentration of the breathing gases are within a safe region or below a safe value. Alternatively, the time delay may be a set time stored in the memory of the controller.

The system/apparatus may be provided with a flow generator. The flow generator may provide a source of gases to a user via the patient interface 16. The flow generator may be located at a suitable place in the system/apparatus (for example in a manner as described previously or herein).

Signals or a control system associated with the apparatus or system or method as described herein may provide for an audible or visual warning or alarm of indicator that a supplementary gas has been reduced or stopped from being supplied to a breathing circuit or to a flow of gases being delivered to the patient. For example, a screen with a graphical user interface (GUI) can provide for an output to indicate the mode that the respiratory support system is in or has switched between or another indicator of the gases being supplied to the patient. Warning alarms, such as audible noises, can also be provided.

Figure 8:
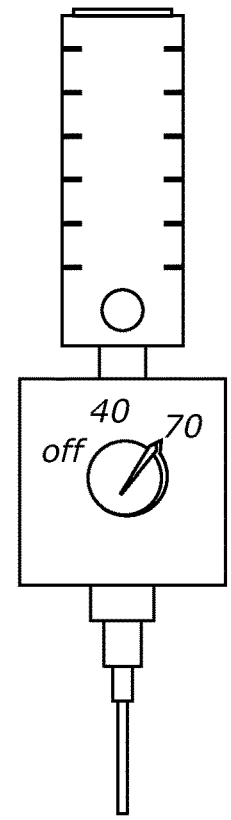
FIG. 8 illustrates a possible flow control device.

In further embodiments, the flow control devices could be cascaded (see, e.g., FIG. 7) so the flow from 2 or 3 flow sources and/or flow control devices can be added together. This could be achieved with a Y-piece 80 (FIG. 7) or any other device that connects and adds flow. Alternatively, the flow control mechanism of the flow device could be replaced with a mechanism that allows 70 L/min or even higher flows. This could include blocking some of all of the original mechanism and adding additional parts to increase capacity. Examples of possible replacements include: New knob and needle that allows 70 L/min; new valve assembly that has a selection of appropriate settings for the therapy. See, for example, FIG. 8 in which an arrangement can be provided with a flow controller that has pre-set flow rates which can be achieved through an electronically controlled valve to open or close the valve as necessary to reach the desired selected flow without the need for a user to manually adjust a valve to obtain the desired flow rate. The flow meter may have one or more pre-set flow rates (e.g. 0 LPM, 30 LPM, 40 LPM or a value likely to meet a patient's inspiratory demand, 70 LPM). These could be actuated with a switch or mechanism with three or more positions that correspond to different pre-set values.

Any of the embodiments described can be used alone or in one or more combinations to preserve gas supplies.

According to the disclosure provided herein, at least one additional embodiment provides for a method of controlling gases delivery to a patient via a patient interface. Such a method comprising receiving an input relating to either a patient's breathing phase and/or another patient parameter, controlling a flow of gases to be delivered to the patient and the inclusion in said flow of gases of a supplementary gas, such that the amount of supplementary gas provided to the patient is substantially synchronized with respect to the patient's breathing phase and/or another patient parameter.

In such a method, the patient can receive (or be delivered) a lesser (or lower) amount of the supplementary gas component during an expiration phase of the patient's breathing phase relative to (that received or delivered during) an inspiration phase of the patient. In the alternative, the patient can receive (or be delivered) a greater amount of the supplementary gas during an inspiration phase of the patient's breathing phase relative to (that received or delivered during) an expiration phase of the patient.

As described previously herein, a patient's breathing phase can be determined by various factors, at least one of which is a measured pressure of a pressure in an airway of the patient, and may alternatively or in addition be those such as a patient's chest movements such as chest compressions using Electrical Impedance Tomography bands (referred to as EIT bands), oxygen saturation of the patient (e.g. via pulse oximeter), or patient CO2 output to provide an indicator of a patient's breathing phase or an exhalation phase of the patient, or one or more pressure sensors may be utilised (e.g. pressure sensors can be used to measure pressure in a patient airway or alternatively measure a differential pressure in the supply tube or conduit to determine the inspiration phase or expiration phase of the patient.

A patient's breathing phase can alternatively or in addition be determined by a measured indicator of a patient's breathing phase. Accordingly, one or more of these may be utilised in combination, or may be utilised in combination with another patient parameter for determining when to provide a supplementary gas to the patient or for inclusion in the flow of gas to be delivered to the patient, or this data may be individually used (i.e. as a sole parameter or input for a controller) or can be used in combinations thereof (e.g. some parameters may have a relative weighting according to what is to be then controlled via a controller, such that when combined the system can provide for control according to a balanced determination of those inputs) to determine the inclusion of the supplementary gas.

The supplementary gas can one or more of: oxygen, helium and oxygen (heliox), anaesthetics, analgesics, nitric oxide, nitrous oxide.

The method can receive input relating to another patient parameter, where the another patient parameter comprises another patient parameter comprising a measurable attribute of a patient.

According to the method as described here, the method can include controlling a valve, such that the valve is actuatable to allow for a supply of the supplementary gas to the system or for inclusion in the flow of gases to be delivered to the patent, during an inspiration phase of the patient's breathing phase.

In one particular mode of operation, the flow of gases to be delivered to the patient can maintained at a substantially constant flow rate throughout different phases of a patient's breathing phases.

In another mode of operation, the flow of gas to be delivered to the patient can be substantially synchronised with a patient's breathing phase or another patient parameter. For example, may be synchronised so as to be phase (e.g. in-phase or matched) with the patient's breathing phase or the another patient parameter.

In another mode of operation, the flow of gases to be delivered to the patient can be of a greater flow rate during a patient's inspiration phase, and of a relatively lower flow rate during a patient's expiration phase.

The flow of gases to be delivered to the patient, for example from a source of gases, can be one or more of: air, a mixture of air and supplementary gas, such but not limited to, a mixture of air and nitrogen.

In another mode of operation, the supplementary gas can be diverted or directed into a reservoir during a patient's expiration phase or when the system determines that supplementary gas does not need to be included in the flow of gases to be delivered to the patient.

When supplementary gas has been diverted or directed into a reservoir during, for example during a patient's expiration phase or according to another patient parameter, or at least a portion of the supplemental gas has been diverted or directed into the reservoir, such supplemental gas in the reservoir can provided or allowed for inclusion in the flow of gases to be delivered to the patient during a patient's inspiration phase or according to another patient parameter.

In some embodiments, an optional flow generator can be utilised. Such a flow generated can be activated or controlled to provide for a flow of the supplementary gas from the reservoir for inclusion in the flow of gases to be delivered to the patient during a patient's inspiration phase or according to another patient parameter. Such a flow generator can be deactivated or controlled to reduce or stop a flow of supplementary gas from being provided from the reservoir for inclusion in the flow of gases to be delivered to the patient during a patient's expiration phase or according to another patient parameter.

In another embodiment, the flow of gases to be delivered to the patient can be of a flow rate that is above the patient's inspiratory demand, such as above the patient's PEAK inspiratory flow (PIF) demand.

In one example the flow of gases delivered to the patient during a patient's inspiration phase is greater than about 40 litres/min and during a patient's expiration phase is below 35 l/min In one example, the flow of gases to be delivered to the patient is greater than about 60 litres/min throughout different phases (i.e. through an inspiratory phase and also an expiratory phase) of a patient's breathing phases and can be kept constant.

In another example, the flow of gases to be delivered to the patient during a patient's inspiration phase can comprise greater (or more) than about 80% supplementary gas (e.g. oxygen) on a flow rate basis of the gas delivered to the patient. Alternatively, the flow of gases to be delivered to the patient during a patient's expiration phase comprises less than about 20% supplementary gas on a flow rate basis of the gas delivered to the patient (i.e. of the total flow rate of gas delivered to the patient, less than about 20% of the flow rate is provided by the supplementary gas). Accordingly, the above alternatives can be combined to provide for a cycling or phasing of the provision of supplementary gas for delivery to the patient or for inclusion in the flow of gases to be delivered to the patient according to the patient's breathing phase or when determined by another patient parameter (e.g. chest movement or other parameters as previously described herein).

Still further, during a patient's inspiration phase, or according to another patient parameter for determining if to provide the supplementary gas, the supplementary gas can be delivered in the form of a bolus (i.e. a discrete amount). That is, a discrete amount can be administered for inclusion in the gas flow to be provided to the patient. Such a bolus can be provided from a source of the supplementary gas, such a source may optionally comprise of a reservoir which may have had supplementary gas diverted or directed previously. For example, when the supplementary gas has been diverted or directed into a reservoir, such as during a patient's expiration phase or according to another patient parameter, then such supplementary gas can be subsequently provided for inclusion in the flow of gases to be delivered to the patient during a patient's inspiration phase or according to another patient parameter.

Under different modes, the flow of gases to be delivered to the patient can be of a flow rate that is greater than about 60 litres/min during a patient's expiration phase to promote a lung recruitment, or for example for a maintenance of a positive end-expiratory pressure (PEEP) to provide for a lung recruitment.

When in another mode, the flow of gases to be delivered to the patient during a patient's inspiration phase can comprise less than about 100% and greater than about 90% of supplementary gas as am amount of the gas to be delivered to the patient. In another mode, the flow of gases to be delivered to the patient during a patient's expiration phase can comprise less than about 30% and greater than about 0% of supplementary gas as an amount of the gas delivered to the patient.

Figure 5F:
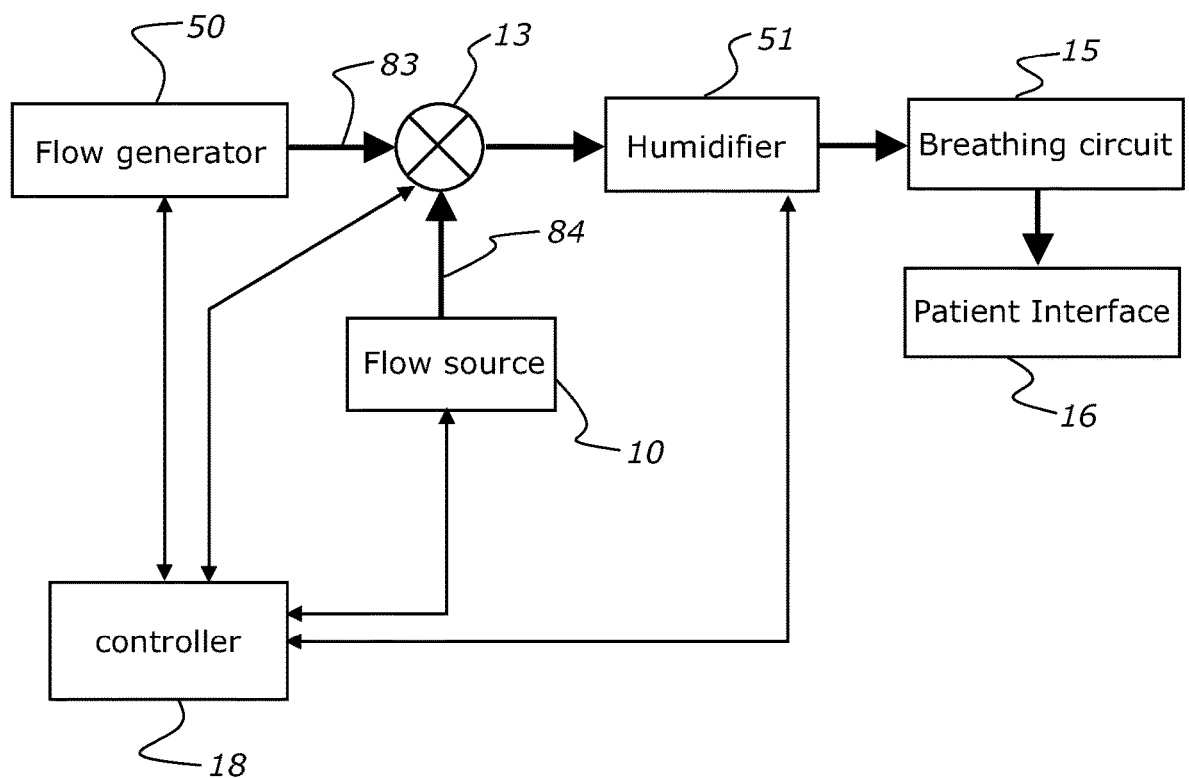
FIG. 5F shows an alternative embodiment to that of FIGS. 5A, B.

According to the disclosure herein, there is provided an apparatus or system to carry out the method as described above. An embodiment of such an apparatus or system is shown in FIG. 5F. The apparatus or system comprises a controller 16. The controller 16 may receive input relating to either a patient's breathing phase and/or another patient parameter (such flow of data is not shown, but ways in which this input can be obtained is described elsewhere in this specification). The controller also controls the operation of other components of the system. Such a controller may be similar to that as described previously.

The system may also comprise a flow generator 50, to provide a flow of gas to be delivered to a patient or patient interface (patient not shown, but would be at an outlet of such a patient interface). The flow generator 50 may be fluidly coupled by a main gas line 83 to a humidifier 51, and/or a breathing circuit 15 and a patient interface 16 (all of which have been described previously). The controller 16 may control the operation of the flow generator 50, to vary the flow rate of gases provided to the breathing circuit 15 and patient interface 16.

The system may also comprise a flow source 10. The flow source 10 being a source of supplementary gas (e.g. oxygen). The flow source 10 and supplementary gas is as described previously herein.

The system also may comprise a valve 13, to control the inclusion of a supplementary gas in the flow of gas to be delivered to a patient. The valve 13 may be coupled to flow source 10 by supplementary gas line 84. The valve 13 can be configured to allow the inclusion of supplementary gases from the flow source 10 into the main gas line 83. Such a valve may be a proportional valve or other type of control valve (for example the various valves as described elsewhere in this specification or as may be suitable to obtaining the intended result described herein.

In the embodiment as shown in FIG. 5F, the valve 13 can be positioned after the flow generator 50 and before an optional humidifier 51. Alternatively or additionally, the valve 13 or other valves can be located at any point in the system. In some embodiments the valve 13 can be located before, or as part of the flow generator 50. In other embodiments, the valve 13 can be located after a provided humidifier 51.

The controller 16 is connected to the valve 13 and controls the valve, such that the amount of supplementary gas provided to the patient is substantially synchronized with respect to the patient's breathing phase and/or another patient parameter.

The system may also comprise an oxygen reservoir located in the system (a reservoir is not shown in FIG. 5F, but may for example be a reservoir of the type described elsewhere in this specification). The oxygen reservoir may be that as described elsewhere in this specification.

According to the disclosure provided herein, at least one additional embodiment provides for an apparatus or system for controlling gas to be delivered to a patient. Such an apparatus or system comprises a gas line connected or connectable to a flow source, a gas reservoir, a patient interface, and a valve. The valve to optionally: fluidly couple, the gas line to the reservoir, and fluidly couple, the gas line and/or reservoir (directly or indirectly) to the patient interface. The apparatus or system further comprises of a controller that receives input relating to either a patient's breathing phase and/or another patient parameter. The controller: during patient expiration, controls the valve to couple the gas line to the reservoir, and during patient inspiration controls the valve to couple the gas line and/or reservoir to (directly or indirectly) the patient interface.

The apparatus or system may additionally comprise of a flow generator, such that the controller during a patient's breathing phase of expiration controls the flow generator to couple gas flow to (directly or indirectly) the patient interface and/or during a patient's breathing phase of inspiration controls the flow generator to couple gas flow to (directly or indirectly) the patient interface.

The flow generator can be controlled to provide for a gas flow to be delivered to the patient interface at or above the patient's inspiratory demand, such as above the patient's PEAK inspiratory flow (PIF) demand.

The flow source can provide for a source of oxygen.

In addition, the apparatus can comprise of a gas line connected or connectable to a flow source, a gas reservoir, and a controller configured to receive input on a patient's breathing phase, the gas line to direct gas flow from a flow source to the gas reservoir during a patient's expiration phase, and directing gas flow from the flow source and/or gas from the reservoir (directly or indirectly) to a patient interface during a patient's inspiration phase.

The reservoir is capable of then delivering a supplementary gas, such as oxygen, to the patient interface during the patient's inspiration phase. Such supplementary gas (e.g. oxygen) can be delivered from the reservoir as a bolus during the patient's inspiration phase or according to another patient parameter.

For example, according to those various embodiments and configurations described herein, a flowrate of gases supplied or provided to an interface or via a system, such as through a flowpath, may comprise, but is not limited to, a flow rate of between about 5 or 10 litres per minute (LPM) and about 100 LPM, or between about 15 LPM and about 95 LPM, or between about 20 LPM and about 90 LPM, or between about 25 LPM and about 85 LPM, or between about 30 LPM and about 80 LPM, or between about 35 LPM and about 75 LPM, or between about 40 LPM and about 70 LPM, or between about 45 LPM and about 65 LPM, or between about 50 LPM and about 60 LPM. For example, according to those various embodiments and configurations described herein, a flow rate of gases supplied or provided to an interface or via a system, such as through a flowpath, may comprise, but is not limited to, flows of at least about 5, 10, 20, 30, 40, 50, 60, 70, 80, 90, 100, 110, 120, 130, 140, 150 L/min, or more, and useful ranges may be selected between any of these values (for example, about 40 to about 80, about 50 to about 80, about 60 to about 80, about 70 to about 100 L/min, about 70 to about 150 lpm, about 80 L/min to about 150 lpm.

Such relatively high flowrates of gases may assist in providing the supplied gases into a user's airway, or to different parts of a user's airway, for example such flowrates may allow for a delivery of such gases to the upper or lower airway regions. Upper airway region typically includes the nasal cavity, pharynx and larynx, while the lower airway region typically includes the trachea, primary bronchi and lungs.

In addition to the various embodiments described above, there is also disclosed a dispensing assembly for delivering surfactant to the airways or lungs of a patient.

Combined with atelectasis prevention, the disclosure herein provides for the ability to, for example during an inspiratory phase of a patient, delivering a supply of gases to a patient comprising about 99% O2 and that is controllable to deliver, during the patient's expiration phase, a lesser amount of O2. In one example, during an inspiration phase of the patient it is possible for the system to control the gases delivered so that a gas flow is provided to the patient comprising greater than about 80% O2, but less than about 100%—in this manner, ensuring that some other gases e.g. Nitrogen remain in the patient's alveoli to help minimise or prevent collapse of the alveoli during the patient's expiration phase. The controlled delivery of a lower O2 fraction of a gas flow during the patient's expiration phase may help reduce the chances of alveoli collapse.

Combined with lung recruitment, the disclosure herein provides for the ability to, for example during an expiratory phase of a patient, delivering a supply of gases to a patient at a flow rate may be set to the same flow rate or a higher flow rate relative to the flow rate provided to the patient during an inspiratory phase in order to help maintain lung recruitment and keep open a patient's airway during the expiratory phase. For example, where the flow rate during an inspiratory flow may be about 30 LPM or about 40 LPM, then at least a portion of the expiratory phase the flow rate delivered to the patient may be maintained or may be increased in order to maintain lung recruitment and PEEP during at least a portion of the patient's expiratory phase. This may for example be useful or have particular application for those patients who may be prone to atelectasis.

In addition to the above, optionally the delivery of a surfactant can be timed to coincide or be synchronous with a patient's breathing phase. For example, a delivery mechanism can be timed to deliver the surfactant during an inspiration phase, or the delivery mechanism can be timed to stop or prevent the delivery of surfactant during a patient's inspiration phase. The stopping or preventing of the delivery during the inspiration phase can be useful for reducing surfactant wastage. In some embodiments, the surfactant can be delivered during a high flow phase of inspiration. A valve mechanism can be positioned on the surfactant delivery mechanism to supply surfactant during inspiration. In this way surfactant can more successfully or effectively delivered or administered into the patient's airways for use in the lungs.

Delivering surfactant to the lungs of a patient can be difficult due to various issues caused by existing delivery methods. Instillation via intubation can be difficult and may cause airway trauma. Effective nebulisation products do not yet exist. Some issues include the action of aerosolization denaturing the surfactant proteins and not being able to achieve the appropriate particle size to avoid "rain out" in the airway and allow penetration deep into the lung.

A first embodiment of the disclosures relates to a dispensing assembly which may be used to deliver surfactant to counteract atelectasis and to compensate for the potential loss of surfactant during anaesthesia or due to other reasons. It enables targeted delivery of surfactant to the lungs of a patient.

Accordingly, there is provided a dispensing assembly for delivering a surfactant to a user, comprising:
 a container for storing the surfactant, the container comprises an opening or an outlet allowing the surfactant to be dispensed from the container, and
 an associated dispensing mechanism configured to cause the container to dispense the surfactant,
 a tube for delivering the surfactant to the patient, the tube comprises a first end which is in fluid communication with the container opening, and a second end which leads into the patient, at the first and/or the second end of the tube there is an orifice which has a dimension configured to cause nebulisation of the surfactant before it is delivered to the patient.

Figure 9A:
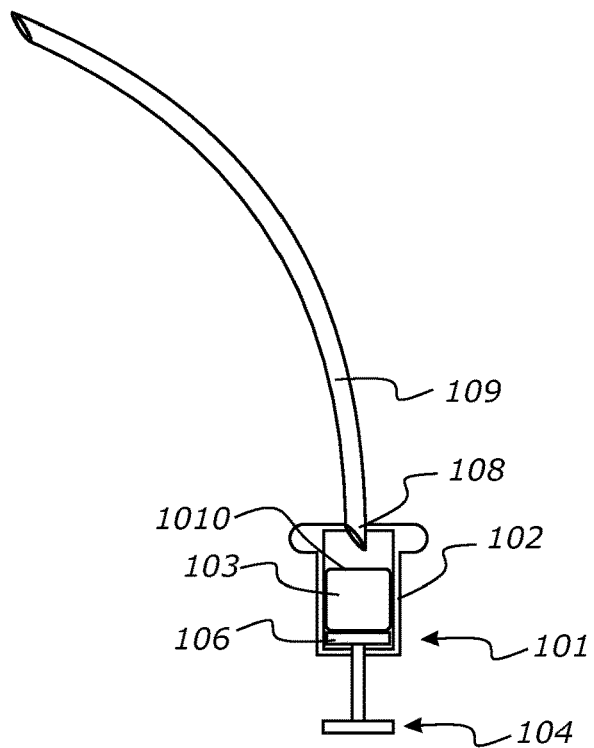
FIGS. 9A and 9B show a dispensing assembly according to the disclosure.
Figure 9B:
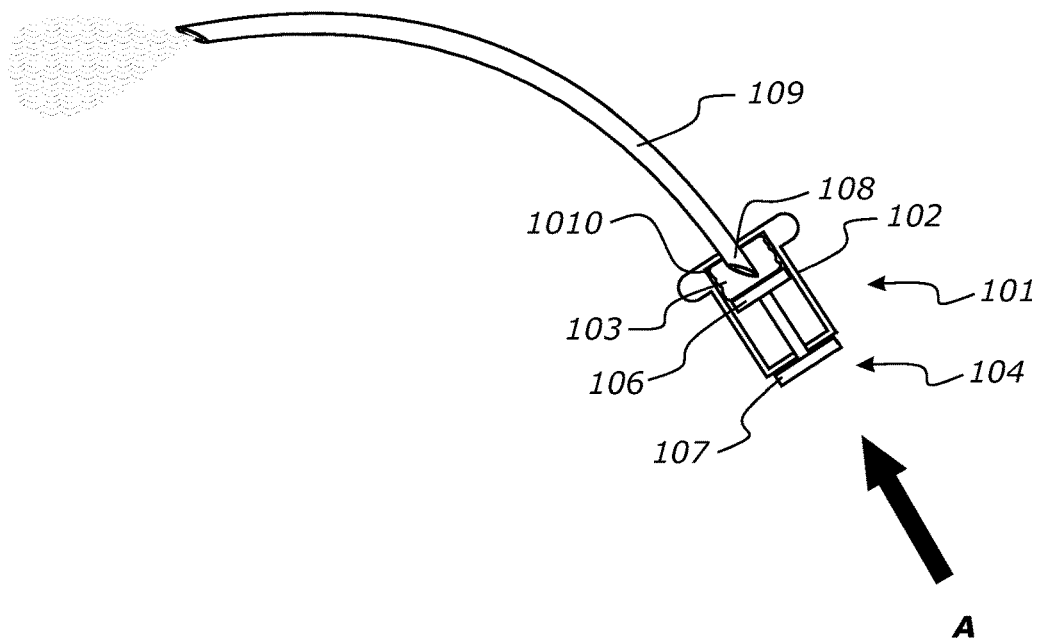

FIGS. 9A and 9B each shows a dispenser 101 according to the first embodiment of the disclosure which may be used to prevent or treat atelectasis by delivering a surfactant to the airways or lungs of a patient.

As shown in the embodiment, the dispenser 101 comprises a container 102 within which the surfactant 103 may be stored, and an associated dispensing mechanism for dispensing the surfactant 103 from the container 102 via an opening 108 near a top portion of the container 102. In this example, the dispensing mechanism comprises a plunger 104 reciprocally received within a lower portion of the container 102 and which is used to dispense surfactant 102 by for example pushing the plunger 104 into the container 102. The plunger 104 comprises a pushing end 106 reciprocally received within the container 102, and a gripping end 107 located outside of the container 102 for a user to grip, and also a connecting portion between the pushing end 106 and the gripping end 107 and which is slidably engaged with a wall of the container 102.

As the plunger 104 is pushed into the container volume as indicated by arrow A, the surfactant 103 is pushed towards the opening 108 of the container 102 and then dispensed out of the container 102. The opening 108 is in fluid communication with a first end of a tube 109, and a second of the tube leads into the nose, or airways, or lungs of a patient to deliver the surfactant 103.

In one configuration, the dispenser 101 may have the surfactant 103 stored in a flexible bag or pouch 1010 in the dispenser. The bag or pouch 1010 may be replaced after each use. As the plunger 104 is pushed into the container 102, the pouch 1010 is also pushed towards the first end of the tube 109. The first end of the tube 109 may be sharpened to more easily pierce through the pouch 1010. As the plunger 104 is pushed into the container 102 further, the pouch 1010 is squeezed further which forces more surfactant 103 to be pushed into the tube 109. According to the disclosure, the orifice at the first end of the tube 109 is dimensioned to cause nebulisation of the surfactant as it is pushed into the tube 109.

Figure 9C:
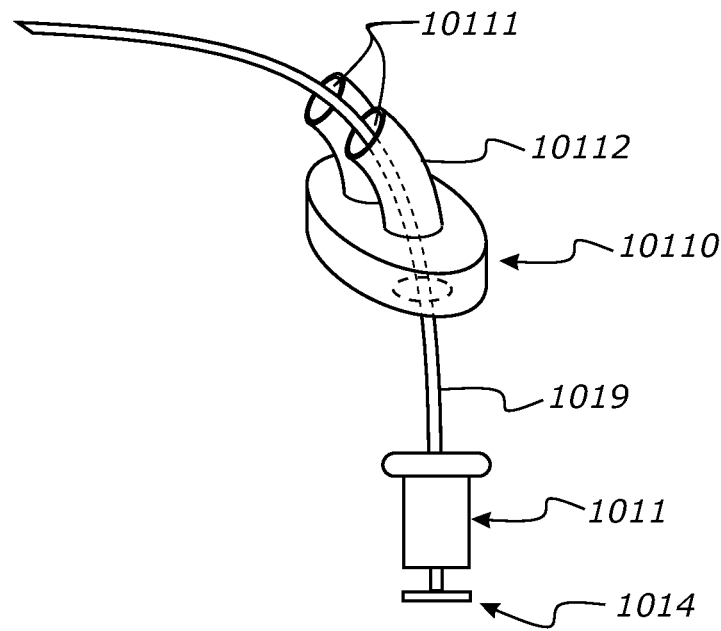
FIG. 9C show a dispensing assembly according to the disclosure.

FIG. 9C shows another configuration. The dispensing assembly may further comprise a nasal interface for example a nasal cannula 1010 configured to be used in combination with the dispenser 101 disclosed above. The nasal cannula 1010 comprises one or two nasal prongs 1012 which extend into the nares of the patient. In this configuration, at least one of the nasal prongs 1012 may be configured and to allow the dispenser tube 109 to pass through and to enter the nasal cavity of a user. The nasal prongs 1012 may be pre-formed into a predetermined shape or angle to help guide the dispenser tube 109 enter the patient's nares. For example, the prongs 1012 may have a bend or curve along its length so that the gas outlets 1011 are pointed towards the back of the nasal cavity of the user. In another form, the nasal prongs 1012 may be made of a flexible material so it can be flexed easily in any direction especially when the tube 109 is inserted into the patient's lungs. In one form, the gas outlets 1011 may comprise a valve (not shown) to prevent gas leak.

Modifications or alterations to interface design or configuration may be provided to allow for improved or greater ease of surfactant delivery.

In one form, the nasal cannula 1010 is used to convey gases such as oxygen, blended gases, or any breathable gases to the user. The gas flow through the nasal interface such as the nasal cannula 1010 may be switched to Heliox (a blend or mixture of helium and oxygen) during surfactant delivery. This may enable surfactant delivery further into the airway due to the reduced airway resistance to flow of Heliox in comparison to normal oxygen.

In a second embodiment, there is provided a method for preventing or treating atelectasis by varying the composition of gases delivered to a user to reduce chance of absorption related atelectasis.

More particularly, in accordance with this second embodiment, there is provided a method of preventing or treating atelectasis comprising the steps of:
 delivering a first concentration of oxygen to a user for a predetermined period, and
 delivering intermittent periods of a second concentration of oxygen to the user, wherein the second oxygen concentration is lower than the first oxygen concentration.

In one form, the first concentration of oxygen may be up to about 100% oxygen, wherein the second oxygen concentration comprises up to about 80% oxygen supplemented with 20% nitrogen (for example, may be about 20% nitrogen), and the second oxygen concentration is delivered to the patient for up to about 5 minutes, or about 3 minutes, or about 1 minute, or up to about 30 seconds, or is about 10-30 seconds of delivery. In another form, the second oxygen concentration may comprise about up to about 80% oxygen supplemented with helium, for example may be about 20% helium, or may be a combination of helium with one or more other gases such as Nitrogen. Heliox has a reduced resistance to flow so the gas composition may be able to enter, and open much smaller alveolar, or partially closed alveolar.

In accordance with the second embodiment described above, there is provided a second method of preventing or treating atelectasis comprising providing a flow of oxygen gases to a user during pre-oxygenation or post-extubation, wherein the oxygen gases has an oxygen concentration of less than 100% or may be even less than about 80%.

The oxygen concentration may be further reduced after a lung recruitment manoeuvre to for example not more than 40%, optionally to increase the time before atelectasis is likely to recur in the patient.

In one form, the oxygen gases are delivered to the user at a higher flow rate so that a lower concentration of oxygen is needed to pre-oxygenate the patient.

The periods of reduced oxygen concentration delivery may be set at regular intervals on a respiratory machine which supplies gases to the patient, for example the machine may be programmed or set to deliver reduced oxygen concentration to the patient every 10 minutes for 10-30 seconds. Alternatively the respiratory machine may have a timer and notify the user that the set period has elapsed and prompt the user to accept the altered gas concentration for a pre-determined or a user-adjustable period.

In various embodiments, the patient's vital signs, such as patient parameters, may also be monitored during the gas delivery, and the gas composition may be automatically adjusted based on monitored results. For example, the respiratory machine may automatically switch back to deliver 100% oxygen to the patient if their $S_pO_2$ falls below 90%. In another embodiment, the machine may allow the user to adjust the oxygen concentration based on their experience, for example a doctor or a nurse may decide to reduce the oxygen concentration level manually by adjusting the machine settings just before extubation to reduce the chance of atelectasis happening on the patient.

The second embodiment as described above, aims to reduce the chance of absorption atelectasis by using a non-oxygen gas such as Helium or Nitrogen to open alveoli, or could be for example other medical gases such as heliox or nitric oxide or a nitrogen and O2 mix or any of the other supplementary gases as described herein. It also provides a more cost effective approach of pre-oxygenation, as a portion of the oxygen is replaced with nitrogen which is a cheaper option than oxygen. Further, the method does not interfere with the other respiratory support therapy being given to the patient as it mainly involves changing the gas compositions delivered to the patient, instead of changing the flow rate of the gases.

Disclosed is also a method of preventing or treating atelectasis by delivering a high flow of oxygen gases during pre-oxygenation and/or intubation.

Current pre-oxygenation methods have problems with delivering reliable pressure support during this phase. A mask and a low flow of oxygen are provided to the patient to pre-oxygenate. The mask generally requires a seal when it is placed on the patient's face which can be difficult to achieve and may need to be removed for various reasons during the pre-oxygenation phase. Removing the mask means losing the seal and therefore the pressure support, potentially allowing alveolar to collapse.

A third embodiment relates to a method of preventing or treating atelectasis by delivering a high flow of oxygen gases during pre-oxygenation intubation attempts.

In one form, a high flow of gases is delivered to for example down a laryngoscope and/or an endotracheal tube.

The high flow of gases delivery may be automatically stopped or turned off and allow the system to deliver respiratory support instead, after intubation has been successful or with settings set up by a user. In one form, a pressure sensor may be located in a cuff of the endotracheal tube to detect when intubation has been successful. Alternatively, a pressure sensor may be located in a valve of the cuff line to close the valve and therefore stops the high flow of gases delivered to the user. The switch from high flow of gases delivery to respiratory support would reduce the risk of hyper-inflation caused by a constant gas flow through a sealed airway.

Figure 10:
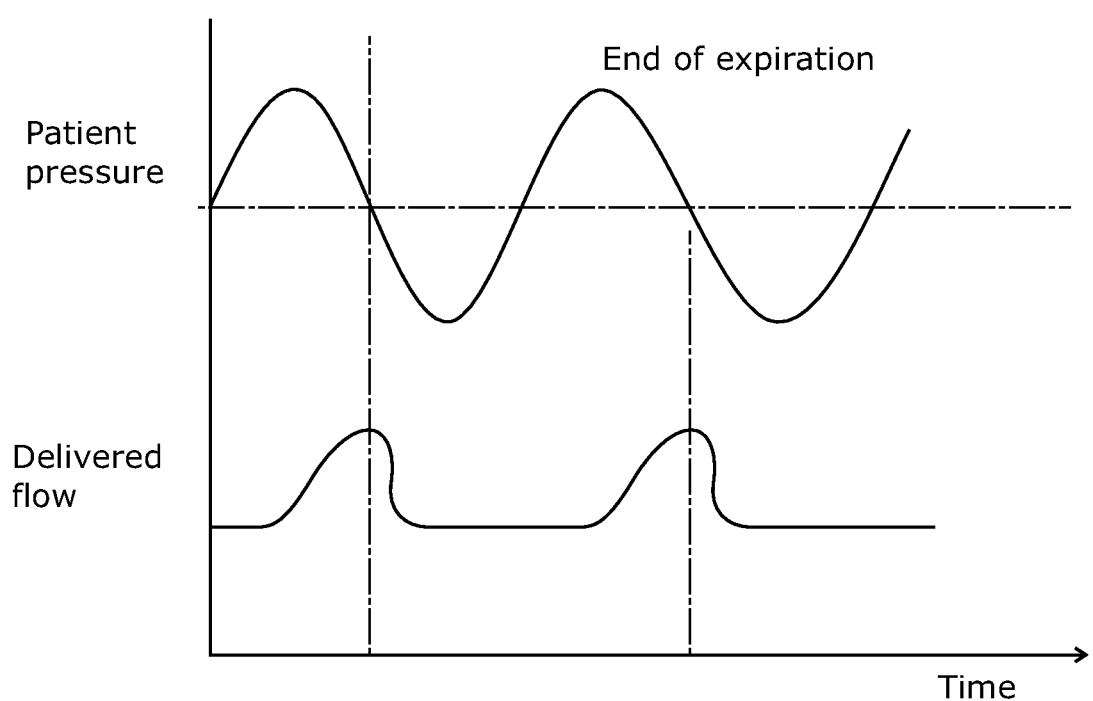
FIG. 10 shows a pressure and flow rate diagram which indicates a higher flow rate may be given to a user at or near the end of an expiration attempt.

In another form, the high flow of gases may be selectively provided to a user at or near the end of an expiration attempt. FIG. 10 shows an increased flow of gases is provided to the patient at or near the end of expiration. If the set delivered flow is low for example less than 60 litres per minute (LPM), or the measured airway pressure is less than a predetermined threshold for example 8 cm H$_2$O, it may be determined that the alveoli are at risk of collapse. If a risk of collapse is determined, the delivered flow may be increased to a pre-determined level for example to 60 LPM near the end of expiration, for example 0.5-1 second before the end of expiration. For example, see FIG. 10 in which the flow may increase relatively gradually towards the end of expiration phase, thereby helping to reduce or prevent sudden pressure changes from being administered or delivered to the patient once then entering an inspiratory phase.

In one form, the airway pressure may be measured for example at cannula prongs using a pressure line alongside or adjacent to nasal prongs.

Interfaces including those such as nasal cannula comprising one or more nasal prongs may be designed or modified to accommodate for a pressure line, including detecting end of expiration point.

This embodiment is aimed to reduce the risk of tissue trauma caused by the opening of collapsed alveoli. If alveoli are opened once collapsed then it may cause tissue trauma. Maintaining patient alveoli also allows maintenance of oxygenation during intubation attempts.

Disclosed is a method or system for performing lung recruitment manoeuvres.

A fourth embodiment relates to a method of preventing and/or treating atelectasis by performing a lung recruitment manoeuvre on the patient. The lung recruitment manoeuvre may be performed by adjusting the flow/pressure of the flow of gases delivered to the patient.

In one form, the flow of gases provided to the patient may have high frequency oscillations of flow/pressure. The oscillations of flow/pressure may contain multiple frequencies, or a broad spectrum.

Figure 11A:
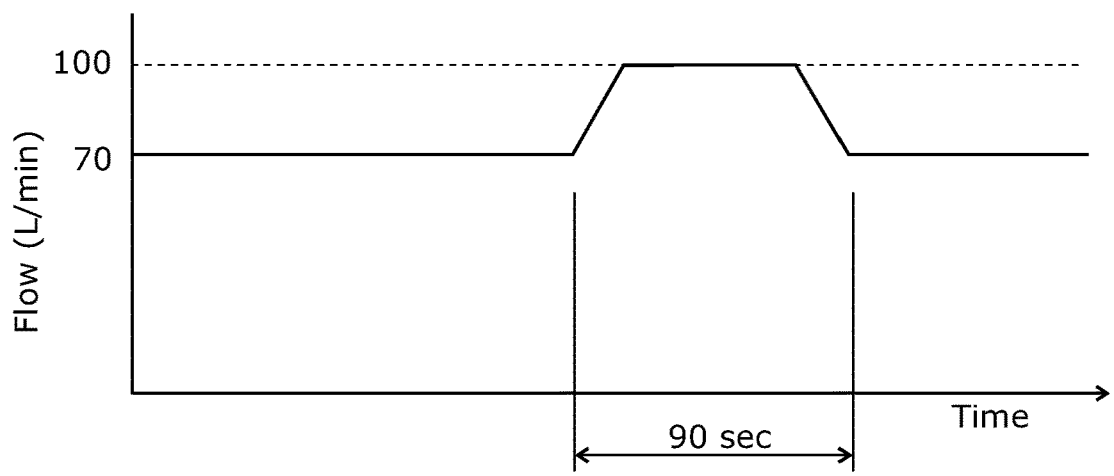
FIGS. 11A-11C each shows an embodiment of a lung recruitment manoeuvre.
Figure 11B:
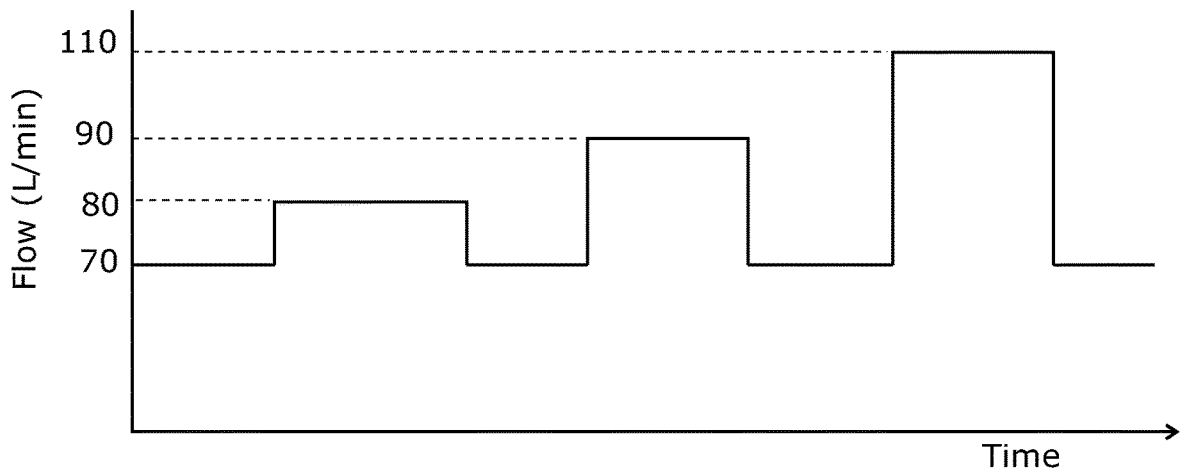

A machine or system may be configured or pre-programmed to deliver such recruitment manoeuvres. FIGS. 11A-11B each shows a flow rate variation diagram which indicates how flow rate or pressure may be adjusted to achieve or encourage lung recruitment.

FIG. 11A shows delivering a higher flow rate of gases to a patient for a set period, for example 100 LPM may be provided to the patient for 90 seconds. 90 seconds may be a sufficient time to distribute the delivered pressure to collapsed lung areas. Different delivery periods may also be chosen depending on the patient's needs. The elevated flow rate may be repeated at predetermined intervals. There may be a period of increase/decrease to the peak flow/pressure to prevent sudden changes in the lung and potential damage.

FIG. 11B shows the gas flow rates may be increased progressively and at set intervals. For example, the flow rate may be first increased to 80 LPM and then hold at this rate for a set time period. It is then reduced to a normal flow rate level of 70 LPM for a period, before it is increased to 90 LPM and then even 110 LPM and then delivered at those rates for a predetermined time period before it returns to 70 LPM again.

Figure 11C:
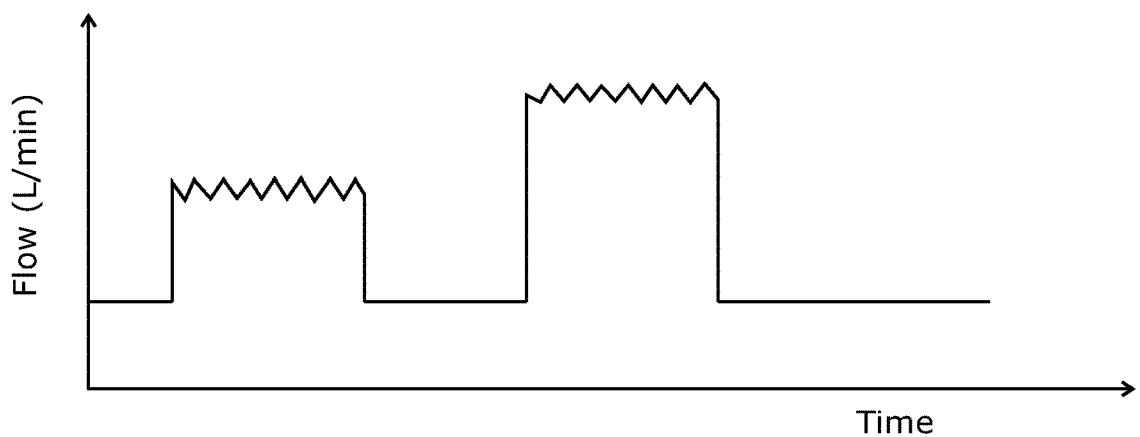

FIG. 11C shows high frequency oscillations super-imposed on increased flow rate may be provided to a patient.

The manoeuvre could be initiated by user (e.g., just before extubation) or could be automatically initiated, or may be recommended or controlled by a respiratory machine during the procedure, for example but not limited to, at set time intervals, or when triggered by a patient monitoring signal. Examples of patient-triggered initiation may include one or a combination of the following:

1. The manoeuvre may be initiated when the measured airway pressure is below a certain threshold as described in embodiment 3 above.
2. The manoeuvre may be initiated when the pressure as measured by the system is below a certain threshold, during supported respiration. This requires the respiratory machine to be connected to a sensing arrangement to receive pressure readings.

3. The manoeuvre may be initiated based on measured patient lung volume and/or area and/or diameter. In one configuration, before the patient is anesthetised, Electrical Impedance Tomography bands (herein: EIT) may be placed around a patient's chest. A 'benchmark' lung volume or chest area/diameter may be measured when the patient is breathing normally. Once the patient is anesthetised any reduction in this measurement may be assumed to be from lung de-recruitment. A lung recruitment manoeuvre may be initiated when the value falls below a certain threshold, for example 90% of full capacity or benchmark value.

4. The manoeuvre may be initiated based on estimated blood oxygen level or $S_pO_2$ of the patient. In one form, if the patient's $S_pO_2$ is not increasing with increasing $FiO_2$, it may be determined that the patient is suffering a diminished respiratory problem, not an oxygen supply problem. This may be caused by atelectasis and thus a recruitment manoeuvre may be useful. In another form, a manoeuvre may be performed regardless of the level of $FiO_2$ currently being supplied to the patient.

The pre-programmed manoeuvre, including maximum flow/pressure, increase or decrease in the flow/pressure, time period or other details may be able to be adjusted or re-programmed by the user.

Device may receive feedback from patient throughout manoeuvre and adjust parameters accordingly. For example if the patient's lung volume and/or area and/or diameter is within a reasonable range or above a threshold, for example if it is above 90% of the predetermined benchmark value then the manoeuvre may be stopped or reduced.

In various embodiments where a set of manoeuvres are given to a patient, the patient's condition may be re-assessed after each manoeuvre.

Once adequate recruitment has been achieved, a lower pressure or flow could be maintained thereafter to prevent recurrent airway collapse. The lower pressure may be for example about 15 cmH2O or the flow may be about 70 LPM.

In various embodiments, the method may be implemented by pre-programming the respiratory machine and therefore the entire process can be automated. This means a user does not have to control respiratory therapy throughout the manoeuvre, the initiation of the manoeuvre can also be automated. The user may be able to use high levels of O2, for example during the pre-oxygenation phase if they are then able to treat any atelectasis that may have formed afterwards.

Disclosed is a lung recruitment device.

A fifth embodiment relates to an interface used for performing lung recruitment manoeuvres. In one form, the interface comprises a seal which can be selectively activated or used to create or form a seal between the user interface and the user's nose and/or mouth. When the seal is formed between the interface and the patient's nose and/or mouth, less gas is leaked out of the system which allows a temporary increase in delivered pressure to aid lung recruitment.

Figure 12A:
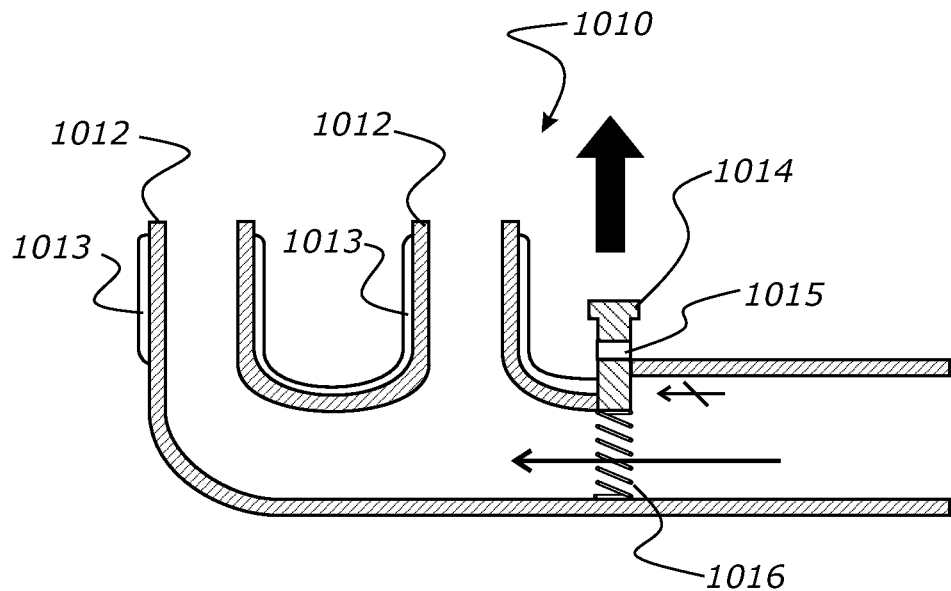
FIGS. 12A and 12B show a user interface which comprises a selectively activated seal.
Figure 12B:
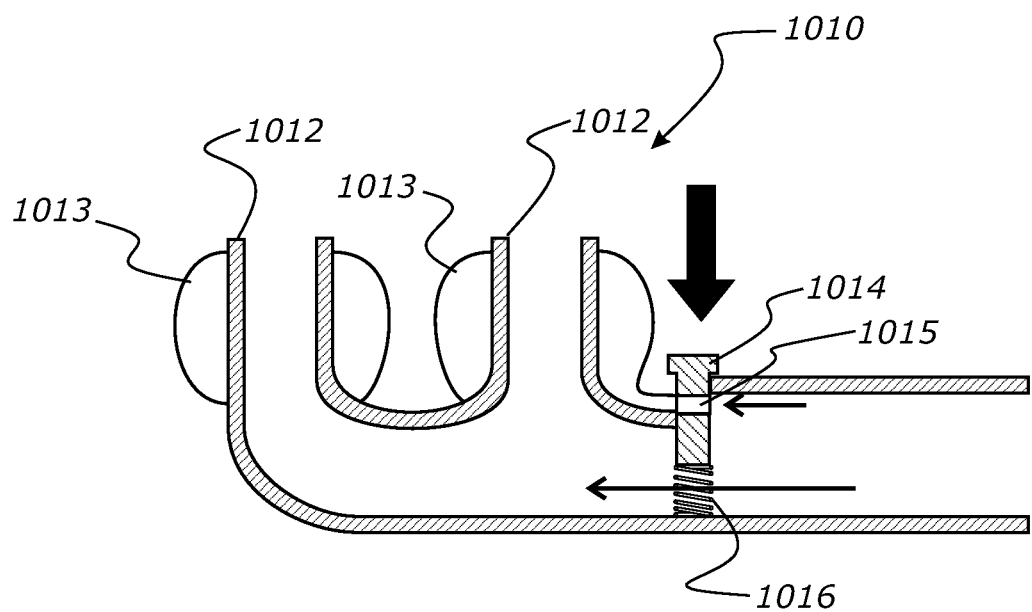

FIGS. 12A and 12B show an exemplary embodiment of such interface which comprises a seal 1013 which can be selectively activated to create or form seal to thereby temporarily increase the pressure delivered to the user. In this example, the interface is a nasal cannula 1010 comprising two nasal prongs 1012 which extend into nares of a patient when in-use. The prongs 1012 generally do not seal against the nares of a patient, which means some gases will be leaked from the prong outlets to the surrounding atmosphere.

In accordance with the disclosures, the nasal prongs 1012 each comprise an inflatable seal 1013 for example on or surrounding the exterior of the prongs 1012. When the seal 1013 is in the deflated state, the nasal prongs 1012 simply extend into the nares of a patient without forming a seal with the nares of the patient. In the inflated state, the seal 1013 inflates, which increases the cross section dimension of the prongs 1012 to allow the prongs 1012 to at least partially occlude the nares and therefore prevent or reduce some of the gas leakage which would otherwise occur without such sealing arrangement.

In the embodiment shown, the seal activation mechanism comprises a plug 1014 which controls the opening and closing of a gas flow path which leads to an interior cavity of the inflatable seal 1013. When the gas flow path is open, gas is directed to flow into the seal interior cavity to inflate the seal 1013. The plug 1014 is biased by a spring 1016 to remain in its generally closed position as shown in FIG. 12A. When the plug 1014 is pushed down as shown in FIG. 12B, an orifice 1015 in the body of the plug 1014 aligns with the gas flow path to create an open pathway for the gases. Once the seal is inflated, the plug 1014 may return to its generally closed position to keep the gases within the seal 1013.

Figure 13A:
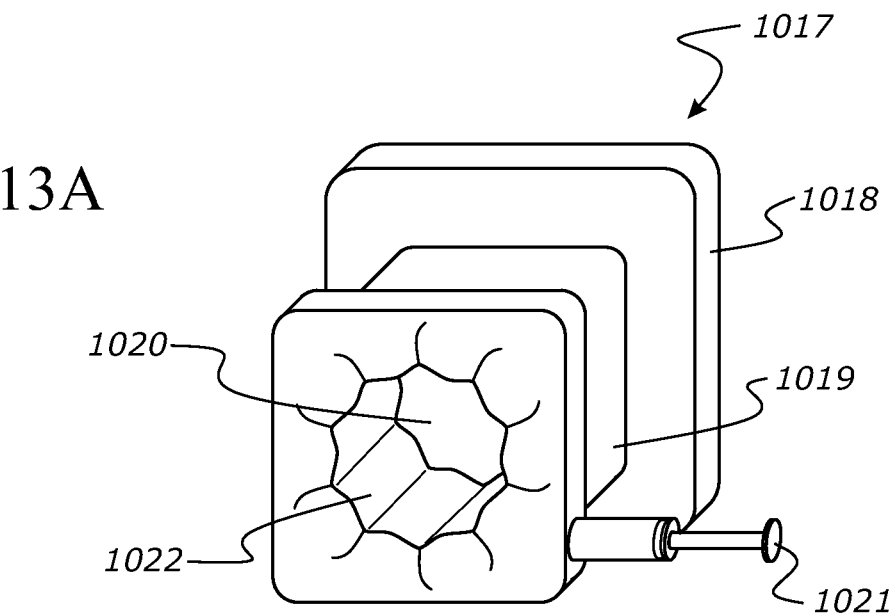
FIGS. 13A and 13B show a second embodiment of a user interface which comprises a selectively activated seal.
Figure 13B:
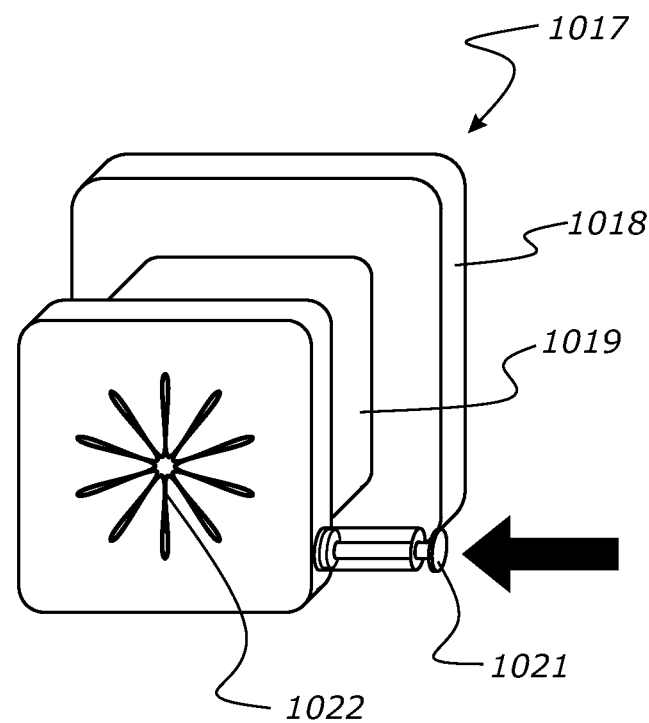

Another user interface which may be used as a lung recruitment device is a mouthpiece, which may be used separately or in conjunction with the nasal cannula of FIGS. 12A and 12B. FIGS. 13A and 13B show an exemplary mouthpiece 1017 which may be a bite-block according to the disclosures. The mouthpiece 1017 comprises a flange 1018 which is to be inserted in the mouth of a user, and which preferably sits behind the teeth of the user when the user closes the mouth; and a biting portion 1019, for the user to bite. The biting-portion 1019 may be formed into a hollow cylindrical shape or other desirable shape, to allow a tube or other airway devices or instruments to be inserted through a passage 1020 formed in the biting portion 1019, or just allow the patient to exhale through the mouthpiece 1017 via the passage 1020.

In this embodiment, the interior of the passage 1020 may also comprise an inflatable seal 1022. The seal 1022 comprises an associated seal activation mechanism controlling the inflation or deflation of the seal 1022. Inflation of the seal 1022 closes or at least reduces the size of the passage 1020. The bite-block 1017 may use a similar seal activation mechanism such as that used in the nasal cannula of FIGS. 12A and 12B. For example, the seal 1022 may be activated by a user pushing a plug 1021 in the direction indicated in FIG. 13B. When such mouthpiece 1017 is used with the nasal cannula of FIGS. 12A and 12B, it prevents or reduces the delivered gas escaping from the mouth which would otherwise reduce the delivered pressure from high flow.

Figure 14A:
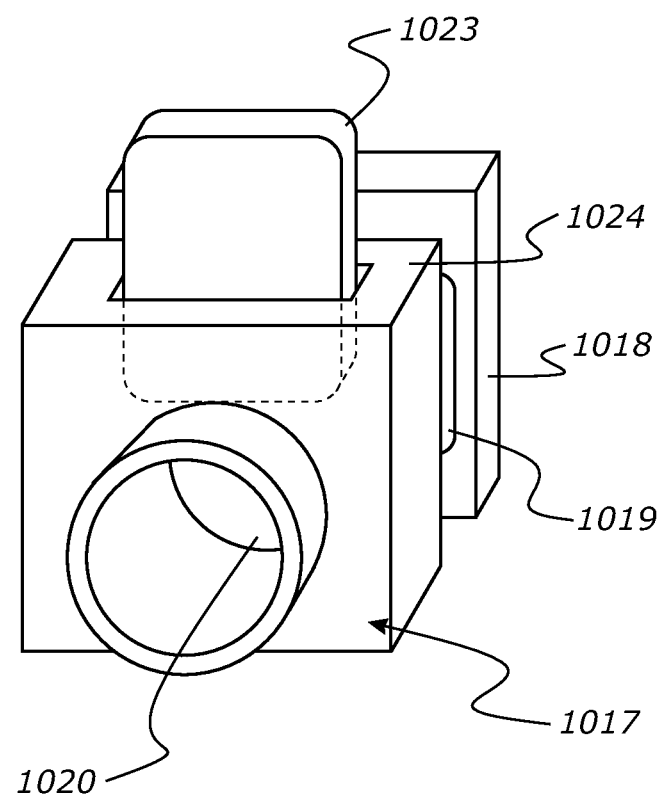
FIGS. 14A and 14B show another embodiment of a user interface which comprises a selectively activated seal.
Figure 14B:
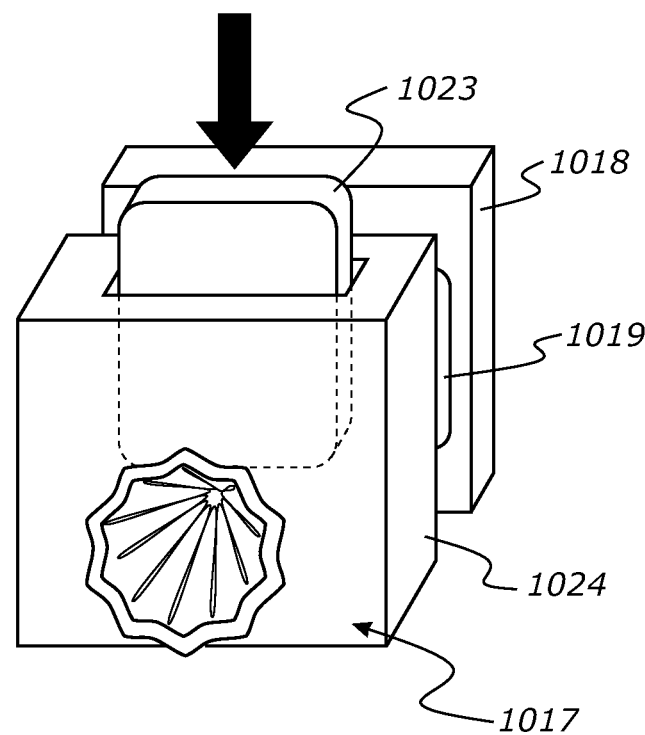

FIGS. 14A and 14B show a different embodiment of a mouthpiece 1017 (for example may be a bite block) which comprises a passage 1020 which is selectively closed or at least reduced in size when the seal activation mechanism is activated. The mouthpiece 1017 has a similar structure as that shown in FIGS. 13A and 13B but uses a different activation mechanism. As shown, the front flange 1024 of the mouthpiece 1017 may comprise a clamp 1023 causes the passage 1020 to close or reduce in size when it is pushed down into a slot of the front flange.

In some configurations, the interface may include a pressure sensor to display pressure to a user. This may be useful in case of constant delivered flow (e.g., high flow) which will cause increasing pressure as flow is left running into a sealed airway.

The various embodiments disclosed herein may be provided in combination with any one or other of the other embodiments or configurations as disclosed here.

The foregoing description of the invention includes preferred forms thereof. Modifications may be made thereto without departing from the scope of the invention.

The invention claimed is:

1. A method of controlling gases delivery to a patient via a non-sealing patient interface, the non-sealing patient interface enabling a leakage of gases to a surrounding atmosphere and providing high flow respiratory support to the patient, the method comprising:
providing high flow respiratory support to the patient through the non-sealing patient interface;
receiving an input relating to a breathing phase of the patient and/or another patient parameter;
controlling a flow of gases to be delivered to the patient and controlling an inclusion in the flow of gases of a supplementary gas;
wherein an amount of the supplementary gas included in the flow of gases is substantially synchronized with respect to the breathing phase of the patient and/or another patient parameter,
wherein the flow of gases receives a lesser amount of the supplementary gas during an expiration phase of the breathing phase of the patient relative to an inspiration phase of the breathing phase of the patient;
wherein the flow of gases delivered to the patient varies dependent upon whether the patient has transitioned between the inspiration phase and the expiration phase of the breathing phase of the patient; and
wherein the supplementary gas is diverted or directed into an expandable reservoir during the expiration phase, and the supplementary gas diverted or directed into the expandable reservoir during the expiration phase is provided for inclusion in the flow of gases delivered to the patient during the inspiration phase.

2. A method of claim 1, wherein the breathing phase of the patient is determined by a measured indicator of the breathing phase of the patient, the measured indicator being one or more of: a pressure in an airway of the patient, a chest movement of the patient, a CO2 measurement in or near an airway of the patient, an oxygen saturation, or output from sensors that detect patient breathing.

3. A method of claim 1, wherein a valve is actuated to allow a supply of the supplementary gas during the inspiration phase of the breathing phase of the patient.

4. A method of claim 1, wherein the flow of gases delivered to the patient is substantially synchronized with the breathing phase of the patient or another patient parameter.

5. A method of claim 1, wherein the flow of gases delivered to the patient is one or more of: air, a mixture of air and supplementary gas, a gas and supplementary gas.

6. A method of claim 1, wherein a flow generator is activated to provide for a flow of the supplementary gas from the expandable reservoir for inclusion in the flow of gases delivered to the patient during the inspiration phase, and the flow generator is deactivated to reduce or stop the flow of supplementary gas from the expandable reservoir from being included in the flow of gases delivered to the patient during the expiration phase.

7. A method of claim 1, wherein the flow of gases delivered to the patient is greater than 60 litres/min throughout different breathing phases.

8. A method of claim 1, wherein the flow of gases delivered to the patient during the inspiration phase comprises greater than about 80% supplementary gas as an amount of the gases delivered to the patient.

9. A method of claim 1, wherein the flow of gases delivered to the patient during the expiration phase comprises less than about 20% supplementary gas as an amount of the gases delivered to the patient.

10. A method of claim 1, wherein the supplementary gas is delivered as a bolus during the inspiration phase.

11. A method of claim 1, wherein the flow of gases delivered to the patient during the inspiration phase comprises less than about 100% and greater than about 90% supplementary gas as an amount of the gases delivered to the patient, and during the expiration phase comprises less than about 30% and greater than about 0% supplementary gas as an amount of the gases delivered to the patient.

12. A method of claim 1, wherein a high flow of oxygen gases above 20 LPM is delivered to the patient during pre-oxygenation intubation attempts.

13. A method of claim 1, comprising delivering high frequency oscillations through respiratory support, wherein high frequency oscillations are at a frequency greater than a breathing frequency of the patient.

14. A method of claim 1, wherein a flow rate during the inspiration phase is above 15 L/min.

15. A method of claim 1, wherein the flow of gases is humidified prior to delivery to the patient.

16. A method of claim 1, wherein the another patient parameter is selected from the group consisting of: whether a source of ignition is detected as being put into operation or has been triggered to turn on for operation, whether a source of ignition is detected as being taken out of operation or has been triggered to turn off from operation, whether a particular device has been detected as being put into or taken out of operation for a procedure to be associated with the patient, and whether a particular device has been triggered to turn on or turn off for a procedure to be associated with the patient.

17. A method of claim 1, wherein the flow of gases comprises oxygen.

18. The method of claim 1 further comprising expanding the expandable reservoir relative to a surface of a face of the patient when the supplementary gas is diverted or directed into the expandable reservoir.

19. The method of claim 1 further comprising expanding expandable bellows of the expandable reservoir that are positioned along a gas supply line when the supplementary gas is diverted or directed into the expandable reservoir.

20. The method of claim 1 further comprising expanding a portion of a gas supply line when the supplementary gas is diverted or directed into the expandable reservoir.

21. A method of controlling a high flow apparatus that controls delivery of gases from one or more flow source through a breathing circuit during an expiration phase and an inspiration phase of a patient, the method comprising:
providing high flow respiratory support to the patient through a non-sealing patient interface;
detecting a breathing phases of the patient and/or another patient parameter;
based upon a detection of expiration or a transition to expiration, storing gases supplied from the one or more flow source during expiration to create one or more volume of stored gases, storing gases comprising delivering gases supplied from the one or more flow source into one or more expandable reservoir;

based upon a detection of inspiration or a transition to inspiration, delivering the stored gases during inspiration, delivering the stored gases comprising directing the stored gases from the one or more expandable reservoir into the breathing circuit in which the stored gases are added to gases from the one or more flow source to provide a first flow rate; and the patient during expiration receiving no flow or a flow of gases less than the first flow rate from a combined flow from the one or more expandable reservoir and the one or more flow source.

22. The method of claim 21 further comprising adding oxygen as the gases.

23. The method of claim 22, wherein the oxygen is added from the one or more expandable reservoir to the breathing circuit as a bolus.

24. The method of claim 23, wherein at least one of the one or more flow source is a constant flow source.

25. The method of claim 24, wherein a valve is positioned between the one or more expandable reservoir and the breathing circuit, and the valve is closed during at least a portion of expiration and opened during at least a portion of inspiration.

26. The method of claim 24, wherein a first valve is positioned between the one or more flow source and the breathing circuit, and the first valve is closed during at least a portion of expiration and opened during at least a portion of inspiration.

27. The method of claim 26, wherein a second valve is positioned between the one or more expandable reservoir and the breathing circuit, and the second valve is closed during at least a portion of expiration and opened during at least a portion of inspiration.

28. The method of claim 24, wherein a valve is positioned between the one or more flow source and the one or more expandable reservoir, and the valve is opened during at least a portion of the expiration phase and closed during at least a portion of the inspiration phase.

29. The method of claim 21, wherein storing gases comprises storing gases in the one or more expandable reservoir as a gas or as a liquid.

* * * * *